(12) United States Patent
Arnold et al.

(10) Patent No.: US 6,358,981 B1
(45) Date of Patent: Mar. 19, 2002

(54) SULPHONAMIDE DERIVATIVES

(75) Inventors: Macklin Brian Arnold, Morgantown; David Michael Bender; Andrew Hendley Fray, both of Indianapolis; Winton Dennis Jones; Paul Leslie Ornstein, both of Carmel; Richard Lee Simon, Greenwood; Hamideh Zarrinmayeh, Carmel; Dennis Michael Zimmerman, Zionsville, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/744,414

(22) PCT Filed: Jul. 28, 1999

(86) PCT No.: PCT/US99/17140

§ 371 Date: Jan. 23, 2001

§ 102(e) Date: Jan. 23, 2001

(87) PCT Pub. No.: WO00/06157

PCT Pub. Date: Feb. 10, 2000

Related U.S. Application Data

(60) Provisional application No. 60/094,905, filed on Jul. 31, 1998.

(51) Int. Cl.[7] .................. C07D 235/04; A61K 31/415

(52) U.S. Cl. .................. 514/331; 514/428; 514/438; 514/461; 514/605; 546/232; 548/570; 549/75; 549/495; 564/97; 564/99

(58) Field of Search .................. 564/97, 99; 514/605, 514/331, 428, 438, 461; 546/232; 548/570; 549/75, 495

(56) References Cited

U.S. PATENT DOCUMENTS

| 4,876,346 A | * 10/1989 | Musser et al. ............... 546/172 |
| 6,174,922 B1 | 1/2001 | Arnold et al. ............... 514/604 |

FOREIGN PATENT DOCUMENTS

| WO | WO 98/33496 | 8/1998 |
| WO | WO00/66546 | 4/1999 |
| WO | WO 00/06083 | 2/2000 |
| WO | WO 00/06148 | 2/2000 |
| WO | WO 00/06158 | 2/2000 |
| WO | WO 00/06159 | 2/2000 |
| WO | WO 00/06537 | 2/2000 |

* cited by examiner

*Primary Examiner*—Zinna Northington Davis
(74) *Attorney, Agent, or Firm*—Nelsen L. Lentz

(57) ABSTRACT

The present invention relates to the potentiation of glutamate receptor function using certain sulphonamide derivatives. It also relates to novel sulphonamide derivatives, to processes for their preparation and to pharmaceutical compositions containing them.

17 Claims, No Drawings

SULPHONAMIDE DERIVATIVES

This is a 371 of PCT/US99/17140 filed Jul. 28, 1999 which claims priority to U.S. Provisional Application No. 60/094,905 filed Jul. 31, 1998.

The present invention relates to the potentiation of glutamate receptor function using certain sulphonamide derivatives. It also relates to novel sulphonamide derivatives, to processes for their preparation and to pharmaceutical compositions containing them.

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the major excitatory pathway in mammals, and is referred to as an excitatory amino acid (EAA). The receptors that respond to glutamate are called excitatory amino acid receptors (EAA receptors). See Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic". This type of receptor has been subdivided into at least three subtypes, which are defined by the depolarizing actions of the selective agonists N-methyl-D-aspartate (NMDA), alpha-amino-3-hydroxy-5-methylisoxazole-4-propionic acid (AMPA), and kainic acid (KA). The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in c-AMP formation, and changes in ion channel function. Schoepp and Conn, *Trends in Pharmacol. Sci.*, 14, 13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacol. Sci.*, 11, 508 (1990); McDonald and Johnson, *Brain Research Reviews*, 15, 41 (1990).

AMPA receptors are assembled from four protein sub-units known as GluR1 to GluR4, while kainic acid receptors are assembled from the sub-units GluR5 to GluR7, and KA-1 and KA-2. Wong and Mayer, *Molecular Pharmacology* 44: 505–510, 1993. It is not yet known how these sub-units are combined in the natural state. However, the structures of certain human variants of each sub-unit have been elucidated, and cell lines expressing individual sub-unit variants have been cloned and incorporated into test systems designed to identify compounds which bind to or interact with them, and hence which may modulate their function. Thus, European patent application, publication number EP-A2-0574257 discloses the human sub-unit variants GluR1B, GluR2B, GluR3A and GluR3B. European patent application, publication number EP-A1-0583917 discloses the human sub-unit variant GluR4B.

One distinctive property of AMPA and kainic acid receptors is their rapid deactivation and desensitization to glutamate. Yamada and Tang, *The Journal of Neuroscience*, September 1993, 13(9): 3904–3915 and Kathryn M. Partin, *J. Neuroscience*, Nov. 1, 1996, 16(21): 6634–6647. The physiological implications of rapid desensitization, and deactivation if any, are unknown.

It is known that the rapid desensitization and deactivation of AMPA and/or kainic acid receptors to glutamate may be inhibited using certain compounds. This action of these compounds is often referred to in the alternative as "potentiation" of the receptors. One such compound, which selectively potentiates AMPA receptor function, is cyclothiazide. Partin et al., *Neuron*. Vol. 11, 1069–1082, 1993. Compounds which potentiate AMPA receptors, like cyclothiazide, are often referred to as ampakines.

International Patent Application Publication Number WO 9625926 discloses a group of phenylthioalkylsulphonamides, S-oxides and homologs which are said to potentiate membrane currents induced by kainic acid and AMPA.

Ampakines have been shown to improve memory in a variety of animal tests. Staubli et al., *Proc. Natl. Acad. Sci.*, Vol. 91, pp 777–781, 1994, Neurobiology, and Arai et al., *The Journal of Pharmacology and Experimental Therapeutics*, 278: 627–638, 1996.

It has now been found that cyclothiazide and certain sulphonamide derivatives potentiate agonist-induced excitability of human GluR4B receptor expressed in HEK 293 cells. Since cyclothiazide is known to potentiate glutamate receptor function in vivo, it is believed that this finding portends that the sulphonamide derivatives will also potentiate glutamate receptor function in vivo, and hence that the compounds will exhibit ampakine-like behavior.

In addition, certain sulfonamide derivatives which potentiate glutamate receptor function in a mammal have been disclosed in International Patent Application Publication WO 98/33496 published Aug. 6, 1998.

Accordingly, the present invention provides a compound of the formula:

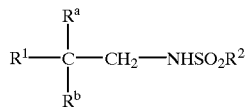

Formula I wherein:
one or both of $R^a$ and $R^b$ are selected independently from F, $CF_3$ and $-OR^c$ wherein $R^c$ is hydrogen or (1–4C) alkyl, and any remainder is hydrogen; or $R^a$ and $R^b$ together represent $=O$ or $=CH_2$;

$R^1$ represents a naphthyl group or a phenyl, furyl, thienyl or pyridyl group which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo(1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydro-thienyl; dihydrofuryl; dihydrothiopyranyl; dihydropyranyl; dihydrothiazolyl; (1–4C)alkoxycarbonyldihydrothiazolyl; (1–4C)alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C) alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, (1–10C)haloalkyl, (1–4C)alkoxycarbonyl(1–4C)alkyl, (1–4C)alkylsulf6nylamino(1–4C)alkyl, (N-(1–4C)alkoxycarbonyl)(1–4C)alkylsulfonylamino(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^2$ represents (1–6C)alkyl, (3–6C)cycloalkyl, (1–6C)fluoroalkyl, (1–6C)chloroalkyl, (2–6C)alkenyl, (1–4C)alkoxy(1–4C)alkyl, phenyl which is unsubstituted or substituted by halogen, (1–4C)alkyl or (1–4C)alkoxy, or a group of formula $R^3R^4N$ in which $R^3$ and $R^4$ each independently represents (1–4C)alkyl or, together with the nitrogen atom to which they are attached form an azetidinyl, pyrrolidinyl, piperidinyl, morpholino, piperazinyl, hexahydroazepinyl or octahydroazocinyl group; or a pharmaceutically acceptable salt thereof.

According to another aspect, the present invention provides a method of potentiating glutamate receptor function in a mammal requiring such treatment, which comprises administering an effective amount of a compound of formula I, or a pharmaceutically acceptable salt thereof as defined herein.

According to another aspect, the present invention provides the use of a compound of formula I, or a pharmaceutically acceptable salt thereof as defined herein for the manufacture of a medicament for potentiating glutamate receptor function.

According to yet another aspect, the present invention provides the use of a compound of formula I or a pharmaceutically acceptable salt thereof as defined herein for potentiating glutamate receptor function.

It is understood that the following compounds of formula Ia and formula Ib are included within the scope of the present invention:

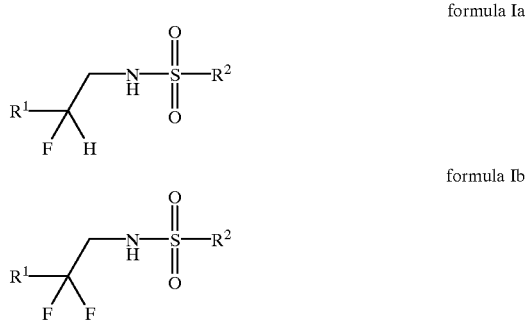

formula Ia formula Ib

More specifically, the following compounds of formula Ic and formula Id are further included within the scope of the present invention:

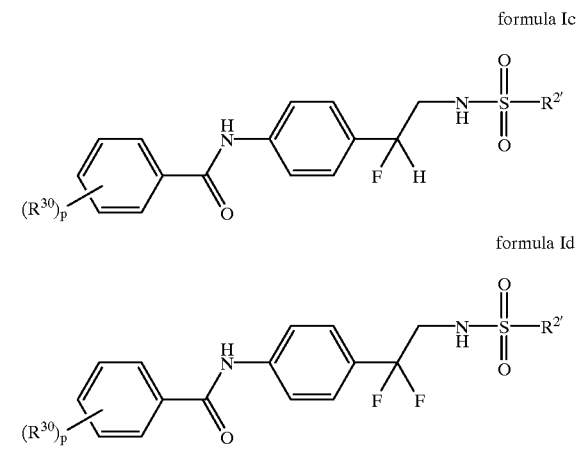

formula Ic formula Id wherein $R^{2'}$ represents (1–4C)alkyl;
$R^{30}$ represents hydrogen, F, Cl, Br, I, CN, $CF_3$, $NH_2$, $NO_2$, $CH_3CONH$, (1–4C) alkyl, (1–4C)alkoxy, and phenyl; and P is 0, 1, 2 or 3; or a pharmaceutically acceptable salt thereof.

In addition, the following compounds of formula Ie and formula If are further included within the scope of the present invention:

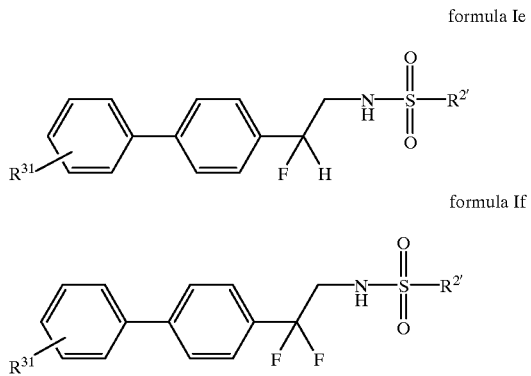

formula Ie formula If wherein $R^{2'}$ represents (1–4C)alkyl; and
$R^{31}$ represents hydrogen, F, Cl, Br, I, CN, $CF_3$, $NH_2$, (1–4C)alkyl, (1–4C)alkoxy), —$(CH_2)NHSO_2R^{2''}$, —(CH$_2$CH$_2$)NHSO$_2$R$^{2''}$, —(CH$_2$CH$_2$CH$_2$) NHSO$_2$R$^{2''}$, —(CH$_2$)NHC(=O)R'', —(CH$_2$CH$_2$)NHC (=O)R'', —(CH$_2$CH$_2$CH$_2$)NHC(=O)R'', —(CH$_2$) NHC(=O)OR'', —(CH$_2$CH$_2$)NHC(=O)OR'', —(CH$_2$CH$_2$CH$_2$)NHC(=O)OR'', wherein R$^{2''}$ represents CF$_3$ or (1–4C)alkyl; or a pharmaceutically acceptable salt thereof.

In addition, the following compounds of formula Ig and formula Ih are included within the scope of the present invention:

formula Ig

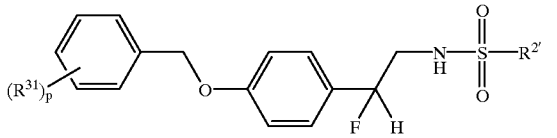

formula Ih

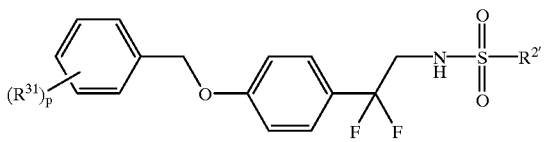

wherein R$^{2'}$ represents (1–4C)alkyl; and

R$^{31}$ represents hydrogen, F, Cl, Br, I, CN, CF$_3$, NH$_2$, (1–4C)alkyl, (1–4C)alkoxy), —(CH$_2$)NHSO$_2$R$^{2''}$, —(CH$_2$CH$_2$)NHSO$_2$R$^{2''}$, —(CH$_2$CH$_2$CH$_2$) NHSO$_2$R$^{2''}$, —(CH$_2$)NHC(=O)R'', —(CH$_2$CH$_2$)NHC (=O)R'', —(CH$_2$CH$_2$CH$_2$)NHC(=O)R'', —(CH$_2$) NHC(=O)OR'', —(CH$_2$CH$_2$)NHC(=O)OR'', —(CH$_2$CH$_2$CH$_2$)NHC(=O)OR'', wherein R$^{2''}$ represents CF$_3$ or (1–4C)alkyl;

P is 0, 1, 2 or 3; or a pharmaceutically acceptable salt thereof.

Preferred values for R$^{2'}$ are methyl, ethyl and isopropyl, with isopropyl being most preferred.

Preferred values for R$^{2''}$ are CF$_3$, methyl, ethyl and isopropyl, with methyl being most preferred.

Preferred values for R$^{30}$ are hydrogen, methyl, ethyl, isopropyl, Fl, Cl, CF$_3$, CH$_3$CONH and CN.

Preferred values for R$^{31}$ are hydrogen, Fl, Cl, CN, methyl, ethyl, isopropyl, CF$_3$, and —(CH$_2$CH$_2$)NHSO$_2$R$^{2''}$.

Preferred values for p are 0, 1 or 2.

It is understood that the compounds of formulas Ia, Ib, Ic, Id, Ie, If, Ig, and Ih, fall within the scope of the formula I.

In this specification, the term "potentiating glutamate receptor function" refers to any increased responsiveness of glutamate receptors, for example AMPA receptors, to glutamate or an agonist, and includes but is not limited to inhibition of rapid desensitisation or deactivation of AMPA receptors to glutamate.

A wide variety of conditions may be treated or prevented by the compounds of formula I and their pharmaceutically acceptable salts through their action as potentiators of glutamate receptor function. Such conditions include those associated with glutamate hypofunction, such as psychiatric and neurological disorders, for example cognitive disorders; neurodegenerative disorders such as Alzheimer's disease; age-related dementias; age-induced memory impairment; movement disorders such as tardive dyskinesia, Hungting-ton's chorea, myoclonus and Parkinson's disease; reversal of drug-induced states (such as cocaine, amphetamines, alcohol-induced states); depression; attention deficit disor-der; attention deficit hyperactivity disorder; psychosis; cognitive deficits associated with psychosis; and drug-induced psychosis. The compounds of formula I may also be useful for improving memory (both short term and long term) and learning ability. The present invention provides the use of compounds of formula I for the treatment of each of these conditions. In addition, the present invention provides the use of the compounds of formula I for treatment of sexual dysfunction.

The term "treating" (or "treat") as used herein includes its generally accepted meaning which encompasses prohibiting, preventing, restraining, and slowing, stopping, or reversing progression, severity, or a resultant symptom.

The present invention includes the pharmaceutically acceptable salts of the compounds defined by formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates or exist in a substantially anhydrous form.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 \times E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formula I can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

As used herein, the term "aromatic group" means the same as "aryl", and includes phenyl and a polycyclic aromatic carbocyclic ring such as naphthyl.

The term "heteroaromatic group" includes an aromatic 5–6 membered ring containing from one to four heteroatoms selected from oxygen, sulfur and nitrogen, and a bicyclic group consisting of a 5–6 membered ring containing from one to four heteroatoms selected from oxygen, sulfur and nitrogen fused with a benzene ring or another 5–6 membered ring containing one to four atoms selected from oxygen, sulfur and nitrogen. Examples of heteroaromatic groups are thienyl, furyl, oxazolyl, isoxazolyl, oxadiazoyl, pyrazolyl, thiazolyl, thiadiazolyl, isothiazolyl, imidazolyl, triazolyl, tetrazolyl, pyridyl, pyridazinyl, pyrimidyl, benzofuryl, benzothienyl, benzimidazolyl, benzoxazolyl, benzothiazolyl, indolyl and quinolyl.

The term (1–10C)alkyl includes (1–8C)alkyl, (1–6C)alkyl and (1–4C)alkyl. Particular values are methyl, ethyl, propyl, isopropyl, butyl, isobutyl, t-butyl, pentyl, hexyl, heptyl, octyl, nonyl and decyl.

The term (2–10C)alkenyl includes (3–10C)alkenyl, (1–8C)alkenyl, (1–6C)alkenyl and (1–4C)alkenyl. Particular values are vinyl and prop-2-enyl.

The term (2–10C)alkynyl includes (3–10C)alkynyl, (1–8C)alkynyl, (1–6C)alkynyl and (3–4C)alkynyl. A particular value is prop-2-ynyl.

The term (1–10C)alkoxy includes (1–6C)alkoxy and further includes (1–4C)alkoxy. Particular values are methoxy, ethoxy, propoxy, butoxy, isopropoxy and isobutoxy.

The term (3–8C)cycloalkyl, as such or in the term (3–8C) cycloalkyloxy, includes monocyclic and polycyclic groups. Particular values are cyclopropyl, cyclobutyl, cyclopentyl, cyclohexyl and bicyclo[2.2.2]octane. The term includes (3–6C)cycloalkyl: cyclopropyl, cyclobutyl, cyclopentyl and cyclohexyl.

The term hydroxy(3–8C)cycloalkyl includes hydroxycyclopentyl, such as 3-hydroxycyclopentyl.

The term oxo(3–8C)cycloalkyl includes oxocyclopentyl, such as 3-oxocyclopentyl.

The term halogen includes fluorine, chlorine, bromine and iodine.

The term halo(1–10C)alkyl includes fluoro(1–10C)alkyl, such as trifluoromethyl and 2,2,2-trifluoroethyl, and chloro (1–10C)alkyl such as chloromethyl.

The term cyano(2–10C)alkenyl includes 2-cyanoethenyl.

The term (2–4C)alkylene includes ethylene, propylene and butylene. A preferred value is ethylene.

The term thienyl includes thien-2-yl and thien-3-yl.

The term furyl includes fur-2-yl and fur-3-yl.

The term oxazolyl includes oxazol-2-yl, oxazol-4-yl and oxazol-5-yl.

The term isoxazolyl includes isoxazol-3-yl, isoxazol-4-yl and isoxazol-5-yl.

The term oxadiazolyl includes [1,2,4]oxadiazol-3-yl and [1,2,4]oxadiazol-5-yl.

The term pyrazolyl includes pyrazol-3-yl, pyrazol-4-yl and pyrazol-5-yl.

The term thiazolyl includes thiazol-2-yl, thiazol-4-yl and thiazol-5-yl.

The term thiadiazolyl includes [1,2,4]thiadiazol-3-yl, and [1,2,4]thiadiazol-5-yl.

The term isothiazolyl includes isothiazol-3-yl, isothiazol-4-yl and isothiazol-5-yl.

The term imidazolyl includes imidazol-2-yl, imidazolyl-4-yl and imidazolyl-5-yl.

The term triazolyl includes [1,2,4]triazol-3-yl and [1,2,4]triazol-5-yl.

The term tetrazolyl includes tetrazol-5-yl.

The term pyridyl includes pyrid-2-yl, pyrid-3-yl and pyrid-4-yl.

The term pyridazinyl includes pyridazin-3-yl, pyridazin-4-yl, pyridazin-5-yl and pyridazin-6-yl.

The term pyrimidyl includes pyrimidin-2-yl, pyrimidin-4-yl, pyrimidin-5-yl and pyrimidin-6-yl.

The term benzofuryl includes benzofur-2-yl and benzofur-3-yl.

The term benzothienyl includes benzothien-2-yl and benzothien-3-yl.

The term benzimidazolyl includes benzimidazol-2-yl.

The term benzoxazolyl includes benzoxazol-2-yl.

The term benzothiazolyl includes benzothiazol-2-yl.

The term indolyl includes indol-2-yl and indol-3-yl.

The term quinolyl includes quinol-2-yl.

The term dihydrothiazolyl includes 4,5-dihydrothiazol-2-yl, and the term (1–4C)alkoxycarbonyldihydrothiazolyl includes 4-methoxycarbonyl-4,5-dihydrothiazol-2-yl.

Examples of values for $R^a$ and $R^b$ are:
for $R^a$: F, $CF_3$ and methoxy
for $R^b$: hydrogen, and
for $R^a$ and $R^b$ together =O and =$CH_2$.

Examples of values for $R^2$ are methyl, ethyl, propyl, 2-propyl, butyl, 2-methylpropyl, cyclohexyl, trifluoromethyl, 2,2,2-trifluoroethyl, chloromethyl, ethenyl, prop-2-enyl, methoxyethyl, phenyl, 4-fluorophenyl, or dimethylamino. Preferably $R^2$ is ethyl, 2-propyl or dimethylamino.

Preferably $R^3$ and $R^4$ each represent methyl.

In the group of formula $(CH_2)_y X^1 R^9$, examples of particular values for y are 0 and 1. $X^1$ preferably represents O, CO, CONH or NHCO. $R^9$ is preferably (1–4C)alkyl, (2–4C)alkenyl, (3–6C)cycloalkyl, pyrrolidinyl, morpholino or tetrahydrofuryl. Examples of values for $R^9$ are hydrogen, methyl, ethyl, propyl, isopropyl, t-butyl, ethenyl, cyclopropyl, cyclobutyl, cyclopentyl, cyclohexyl, 2-pyrrolidinyl, morpholino or 2-tetrahydrofuryl.

Particular values for the group $(CH_2)_y X^1 R^9$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C)alkenyloxy, such as prop-2-enyloxy; (3–10C)alkynyloxy, including (3–6C) alkynyloxy, such as prop-2-ynyloxy; and (1–6C)alkanoyl, such as formyl and ethanoyl.

Preferably the group $(CH_2)_y X^1 R^9$ represents CHO; $COCH_3$, $OCH_3$; $OCH(CH_3)_2$; $NHCOR^9$ in which $R^9$ represents methyl, ethyl, isopropyl, t-butyl, ethenyl, cyclopropyl, cyclobutyl, cyclopentyl, cyclohexyl, 2-pyrolidinyl or morpholino; $CONHR^9$ in which $R^9$ represents cyclopropyl or cyclopentyl; $NHCOCOOCH_3$; or 2-tetrahydrofurylmethoxy.

In the group of formula $(CH_2)_z X^3 R^{15}$, examples of particular values for z are 0, 1, 2 and 3. z is preferably 0. $X^3$ preferably represents O, CO, CONH or NHCO. Examples of values for $R^{15}$ are hydrogen, methyl, ethyl, propyl, isopropyl, butyl, t-butyl, benzyl, 2,2,2-trifluoroethyl, 2-methoxycarbonylethyl, cyclohexyl, 10-camphoryl, phenyl, 2-fluorophenyl, 3-fluorophenyl, 2-trifluoromethylphenyl, 4-trifluoromethylphenyl, 2-methoxyphenyl, 3-methoxyphenyl, 4-methoxyphenyl, 1-(5-dimethylamino)naphthyl, and 2-thienyl.

Particular values for the group $(CH_2)_z X^3 R^{15}$ include (1–10C)alkoxy, including (1–6C)alkoxy and (1–4C)alkoxy, such as methoxy, ethoxy, propoxy, isopropoxy and isobutoxy; (3–10C)alkenyloxy, including (3–6C)alkenyloxy, such as prop-2-enyloxy; (3–10C) alkynyloxy, including (3–6C) alkynyloxy, such as prop-2-ynyloxy; and (1–6C) alkanoyl, such as formyl and ethanoyl.

Preferably the group $(CH_2)_z X^3 R^{15}$ represents $NH_2$; $CH_2NH_2$; $(CH_2)_2NH_2$; $(CH_2)_3NH_2$; $CONH_2$; $CONHCH_3$; $CON(CH_3)_2$; $N(C_2H_5)_2$; $CH_2OH$; $CH(OH)CH_3$; $CH(OH)CH_2CH_3$; CHO; $COCH_3$; COOH; $COOCH_3$; $CH_2NHCOOC(CH_3)_3$; $(CH_2)_2NHCOOC(CH_3)_3$; $NHSO_2CH(CH_3)_2$; a group of formula $(CH_2)_2NHSO_2R^{15}$ in which $R^{15}$ represents $CH_3$, $CH_2CH_3$, $CH(CH_3)_2$, $(CH_2)_2CH_3$, $(CH_3)_3CH_3$, benzyl, $CH_2CF_3$, 2-methoxycarbonylethyl, cyclohexyl, 10-camphoryl, phenyl, 2-fluorophenyl, 4-fluorophenyl, 2-trifluoromethylphenyl, 4-trifluoromethylphenyl, 4-methoxyphenyl, 1-(2-dimethylamino)naphthyl or 2-thienyl; $CH(OH)CH_2NHSO_2CH_3$; $(CH_2)_3NHSO_2CH(CH_3)_2$; $COCH_2N(OCOC(CH_3)_3)SO_2CH_3$; $COCH_2NHSO_2CH_3$; $(CH_2)_2NHCOR^{15}$ in which $R^{15}$ represents $CH_3$, $CH(CH_3)_2$, $CH_2CH(CH_3)_2$, phenyl, 3-fluorophenyl, 4-fluorophenyl, benzyl, 2-methoxyphenyl, 4-methoxyphenyl, 2-thienyl, CH=CH, CH=CHCN, $OCH_3$ or $O(CH_2)_3CH_3$.

In the group of formula $R^{14}$—$(L^a)_n$—$X^2$—$(L^b)_m$, $L^a$ and $L^b$ preferably each independently represents $CH_2$. $X^2$ preferably represents a bond, O, NH, CO, CH(OH), CONH, NHCONH or $OCH_2CONH$. Examples of particular values for $(L^a)_n$—$X^2$-$(L^b)_m$ are a bond, O, NH, S, SO, $SO_2$, CO, $CH_2$, $COCH_2$, COCONH, $CH(OH)CH_2$, CONH, NHCO, NHCONH, $CH_2O$, $OCH_2$, $OCH_2CONH$, $CH_2NH$, $NHCH_2$ and $CH_2CH_2$.

$R^{14}$ is preferably an unsubstituted or substituted phenyl, naphthyl, furyl, thienyl, isoxazolyl, thiazolyl, tetrazolyl, pyridyl, pyrimidyl benzothienyl or benzothiazolyl group.

Examples of particular values for $R^{14}$ are phenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 4-iodophenyl, 2,3-difluorophenyl, 2,4-difluorophenyl, 3,4-dichlorophenyl, 3,5-dichlorophenyl, 4-cyanophenyl, 3-nitrophenyl, 4-hydroxyiminophenyl, 2-methylphenyl, 4-methylphenyl, 4-ethylphenyl, 3-propylphenyl, 4-t-butylphenyl, 2-prop-2-enylphenyl, 4-(4-(1,1-dioxotetrahydro-1,2-thiazinyl)phenyl, 2-trifluoromethylphenyl, 3-trifluoromethylphenyl, 4-trifluoromethylphenyl, 2-bromomethylphenyl, 2-fluoro-4-trifluoromethylphenyl, 4-(2-cyanoethenyl)phenyl, 4-hydroxyphenyl, 2-formylphenyl, 3-formylphenyl, 4-formylphenyl, 2-acetylphenyl, 3-acetylphenyl, 4-acetylphenyl, 2-propanoylphenyl, 2-(2-methyl-propanoyl)phenyl, 2-methoxyphenyl, 3-methoxyphenyl, 4-methoxyphenyl, 4-butoxyphenyl, 2-hydroxymethylphenyl, 4-hydroxymethylphenyl, 2-(1-hydroxyethyl)phenyl, 3-(1-hydroxyethyl)phenyl, 4-(1-hydroxyethyl)phenyl, 2-(1-hydroxypropyl)phenyl, 4-(1-hydroxypropyl)phenyl, 2-(1-hydroxy-2,2-dimethyl-propyl)phenyl, 4-trifluoromethoxyphenyl, 2-aminophenyl,4-aminophenyl, 4-N,N-diethylaminophenyl, 4-aminomethylphenyl, 4-(2-aminoethyl)phenyl, 4-(3-aminopropyl)phenyl, 4-carboxyphenyl, 4-carbamoylphenyl, 4-N-methylcarbamoylphenyl, 4-N,N-dimethylcarbamoylphenyl, 2-isopropylaminomethylphenyl, 4-t-butoxycarbonylaminomethylphenyl, 4-(2-isopropoxycarboxamido)ethylphenyl, 4-(2-t-butoxycarboxamido)ethylphenyl, 4-isopropylsulfonylaminophenyl, 4-(2-methanesulfonylamino)ethylphenyl, 4-(2- ethylsulfonylamino)ethylphenyl, 4-(3-isopropylsulfonylamino)propylphenyl, 4-(1-(2-(2-propane)sulfonylamino)propyl)phenyl, 4-(2-propylsulfonylamino)ethylphenyl, 4-(2-isopropylsulfonylamino)ethylphenyl, 4-(2-butylsulfonylamino)ethylphenyl, 4-(1-isopropylsulfonylaminomethyl)ethylphenyl, 4-(1-hydroxy-2-methanesulfonylamino)ethylphenyl, 4-(2-(2,2,2-trifluoroethyl)sulfonylaminoethyl)phenyl, 4-(2-cyclohexylsulfonylamino)ethylphenyl, 4-(2-(2,2,2-trifluoroethyl)sulfonylamino)ethylphenyl, 4-(2-N,N-dimethylaminosulfonylamino)ethylphenyl, 4-(2-phenylsulfonylaminoethyl)phenyl, 4-(2-(2-fluorophenyl)sulfonylaminoethyl)phenyl, 4-(2-(4-fluorophenyl)sulfonylaminoethyl)phenyl, 4-(2-(2-trifluoromethylphenyl)sulfonylaminoethyl)phenyl, 4-(2-(4-trifluoromethylphenyl)sulfonylaminoethyl)phenyl, 4-(2-(4-methoxyphenyl)sulfonylaminoethyl)phenyl, 4-(2-(1-(5-dimethylamino)napthalenesulfonylamino)ethyl)phenyl, 4-(2-(2-thienyl)sulfonylamino)ethyl)phenyl, 4-(2-benzamidoethyl)phenyl, 4-(2-(4-fluorobenzamido)ethyl)phenyl, 4-(2-(3-methoxybenzamido)ethyl)phenyl, 4-(2-(3-fluorobenzamido)ethyl)phenyl, 4-(2-(4-methoxybenzamido)ethyl)phenyl, 4-(2-(2-methoxybenzamido)ethyl)phenyl, 4-(1-(2-(2-methoxycarbonylethanesulfonylamino)ethyl)phenyl, 4-(1-(2-(10-amphorsulfonylamino)ethyl)phenyl, 4-(1-(2-(benzylsulfonylmino)ethyl)phenyl, 4-(2-phenylacetamido)ethyl)phenyl, 4-methanesulfonylaminoethanoylphenyl, 4-(N-(t-butoxycarbonyl)methanesulfonylaminoethanoyl)phenyl, 4-(2-(2-thienylcarboxamido)ethyl)phenyl, thien-2-yl, 5-hydroxymethylthien-2-yl, 5-formylthien-2-yl, thien-3-yl, 5-hydroxymethylthien-3-yl, 5-formylthien-3-yl, 2-bromothien-3-yl, fur-2-yl, 5-nitrofur-2-yl, fur-3-yl, isoxazol-5-yl, 3-bromoisoxazol-5-yl, isoxazol-3-yl, 5-trimethylsilylisoxazol-3-yl, 5-methylisoxazol-3-yl, 5-hydroxymethylisoxazol-3-yl, 5-methyl-3-phenylisoxazol-4-yl, 5-(2-hydroxyethyl)isoxazol-3-yl, 5-acetylisoxazol-3-yl, 5-carboxyisoxazol-3-yl, 5-N-methylcarbamoylisoxazol-3-yl, 5-methoxycarbonylisoxazol-3-yl, 3-bromo[1,2,4]oxadiazol-5-yl, pyrazol-1-yl, thiazol-2-yl, 4-hydroxymethylthiazol-2-yl, 4-methoxycarbonylthiazol-2-yl, 4-carboxythiazol-2-yl, imidazol-1-yl, 2-sulfhydrylimidazol-1-yl, [1,2,4]triazol-1-yl, tetrazol-5-yl, 2-methyltetrazol-5-yl, 2-ethyltetrazol-5-yl, 2-isopropyltetrazol-5-yl, 2-(2-propenyl)tetrazol-5-yl, 2-benzyltetrazol-5-yl, pyrid-2-yl, 5-ethoxycarbonylpyrid-2-yl, pyrid-3-yl, 6-chloropyrid-3-yl, pyrid-4-yl, 5-trifluoromethylpyrid-2-yl, 6-chloropyridazin-3-yl, 6-methylpyridazin-3-yl, 6-methoxypyrazin-3-yl, pyrimidin-5-yl, benzothien-2-yl, benzothiazol-2-yl, and quinol-2-yl.

Examples of an unsubstituted or substituted aromatic or heteroaromatic group represented by $R^1$ are unsubstituted or substituted phenyl, furyl, thienyl (such as 3-thienyl) and pyridyl (such as 3-pyridyl.

Preferably, $R^1$ represents 2-naphthyl or a group of formula

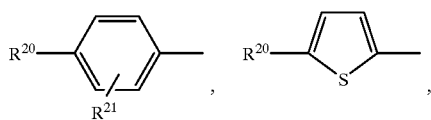

-continued

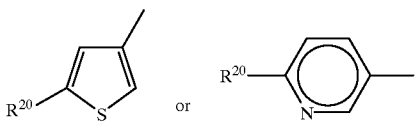

in which
$R^{20}$ represents halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo (3–8C)cycloalkyl; halo(1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$, $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; tetrazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyldihydrothiazolyl; (1–4C) alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; benzothiazolyl; and a group of formula $R^{14}-(L_a)_n-X^2-(L^b)_m$ in which $X^2$ represents a bond, O, NH, S, SO, $SO_2$, CO, CH(OH), CONH, NHCONH, NHCOO, COCONH, $OCH_2CONH$ or CH=CH, NHCO, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; (1–10C)alkyl; (2–10C)alkenyl; (2–10C)alkynyl; (3–8C)cycloalkyl; 4-(1,1-dioxotetrahydro-1,2-thiazinyl); halo(1–10C) alkyl; cyano(2–10C)alkenyl; phenyl; $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, (1–10C)haloalkyl, (1–4C)alkoxycarbonyl(1–4C)alkyl, (1–4C) alkylsulfonylamino(1–4C)alkyl, (N-(1–4C)alkoxycarbonyl)(1–4C)alkylsulfonylamino(1–4C)alkyl, (3–10C)alkenyl, (3–10C)alkynyl, (3–8C) cycloalkyl, camphoryl or an aromatic or heteroaromatic group which is unsubstituted or substituted by one or two of halogen, (1–4C)alkyl, (1–4C)haloalkyl, di(1–4C)alkylamino and (1–4C)alkoxy, and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{21}$ represents a hydrogen atom, a halogen atom, a (1–4C)alkyl group or a (1–4C)alkoxy group.

Examples of particular values for $R^{20}$ are fluorine, chlorine, bromine, cyano, hydroxyimino, methyl, ethyl, propyl, 2-propyl, butyl, 2-methylpropyl, 1,1-dimethylethyl, cyclopentyl, cyclohexyl, 3-hydroxycyclopentyl, 3-oxocyclopentyl, methoxy, ethoxy, propoxy, 2-propoxy, acetyl, acetylamino, ethylcarboxamido, propylcarboxamido, 1-butanoylamino, t-butylcarboxamido, acryloylamido, 2-pyrrolidinylcarboxamido, 2-tetrahydrofurylmethoxy, morpholinocarboxamido, methyloxalylamido, cyclopropylcarboxamido, cyclobutylcarboxamido, cyclopentylcarboxamido, cyclohexylcarboxamido, cyclopropylcarbamoyl, cyclopentylcarbamoyl, pyrrolidin-1-yl, morpholino, piperidin-1-yl, N-methylpiperazinyl, N-benzylpiperazinyl, 2-thienyl, 3-thienyl, 2-furyl, 3-furyl, isoxazol-3-yl, thiazol-2-yl, tetrazol-5-yl, pyrid-2-yl, pyrid-3-yl, pyrid-4-yl, pyrimidin-5-yl, 4,5-dihydrothiazol-2-yl, 4,5-dihydro-4-methoxycarbonylthiazol-2-yl, 4,5-dihydro-4-methoxycarbonyl-5,5-dimethylthiazol-2-yl, benzothien-2-yl, benzothiazol-2-yl, phenyl, 4-hydroxyphenyl, 2-fluorophenyl, 3-fluorophenyl, 2,3-difluorophenyl, 4-chlorophenyl, 3,4-dichlorophenyl, 3,5-dichlorophenyl, 3-nitrophenyl, 4-cyanophenyl, 2-methylphenyl, 4-methylphenyl, 4-(4-(1,1-dioxotetrahydro-1,2-thiazinyl) phenyl, 3-trifluoromethylphenyl, 4-trifluoro-methylphenyl, 4-(2-cyanoethenyl)phenyl, 2-formylphenyl, 3-formylphenyl, 4-formylphenyl, 3-acetylphenyl, 4-acetylphenyl, 4-carboxyphenyl, 2-methoxyphenyl, 4-methoxyphenyl, 2-hydroxymethylphenyl, 4-hydroxymethylphenyl, 3-(1-hydroxyethyl)phenyl, 4-(1-hydroxyethyl)phenyl, 4-(1-hydroxypropyl)phenyl, 2-aminophenyl, 4-aminophenyl, 4-N,N-diethylaminophenyl, 4-aminomethylphenyl, 4-(2-aminoethyl)phenyl, 4-(3-aminopropyl)phenyl, 4-(2-acetylaminoethyl)phenyl, 4-t-butoxycarboxylaminoethyl) phenyl, 4-(2-t-butoxycarboxylaminoethyl)phenyl, benzylsulfonylamino, 4-isopropylsulfonylaminophenyl, 4-(2-methanesulfonylaminoethyl)phenyl, 4-(2-ethylsulfonylaminoethyl)phenyl, 4-(2-propylsulfonylaminoethyl)phenyl, 4-(2-butylsulfonylaminoethyl)phenyl, 4-(2-isopropylsulfonylaminoethyl)phenyl, 4-(1-hydroxy-2-methanesulfonylaminoethyl)phenyl, 4-(2-dimethylaminosulfonylaminoethyl)phenyl, 4-(1-(2-(2-propyl)sulfonylaminopropyl)phenyl, 4-(2-(2,2,2-trifluoroethyl)sulfonylaminoethyl)phenyl, 4-(2-cyclohexylsulfonylaminoethyl)phenyl, 4-(2-phenylsulfonylaminoethyl)phenyl, 4-(2-(2-fluorophenyl) sulfonylaminoethyl)phenyl, 4-(2-(4-fluorophenyl) sulfonylaminoethyl)phenyl, 4-(2-(2-trifluoromethylphenyl) sulfonylaminoethyl)phenyl, 4-(2-(4-trifluoromethylphenyl) sulfonylaminoethyl)phenyl, 4-(2-(4-methoxyphenyl) sulfonylaminoethyl)phenyl, 4-(2-(1-(5-dimethylamino) napthalenesulfonylamino)ethyl)phenyl, 4-(2-(2-thienyl) sulfonylamino)ethyl)phenyl, 4-(2-benzamidoethyl)phenyl, 4-(2-(4-fluorobenzamido)ethyl)phenyl, 4-(2-(3-methoxybenzamido)ethyl)phenyl, 4-(2-(3-fluorobenzamido)ethyl)phenyl, 4-(2-(4-methoxybenzamido) ethyl)phenyl, 4-(2-(2-methoxybenzamido)ethyl)phenyl, 4-(2-(2-thienylcarboxamido)ethyl)phenyl, 4-carbamoylphenyl, 4-methylcarbamoylphenyl, 4-dimethylcarbamoylphenyl, 4-(2-(2-methylpropaneamido) ethyl)phenyl, 4-(2-(3-methylbutaneamido)ethyl)phenyl, benzoylmethyl, benzamido, 2-fluorobenzamido, 3-flurobenzamido, 4-fluorobenzamido, 2,4-difluorobenzamido, 3-chlorobenzamido, 4-chlorobenzamido, 4-bromobenzamido, 4-iodobenzamido, 4-cyanobenzamido, 3-methylbenzamido, 4-methylbenzamido, 4-ethylbenzamido, 4-propylbenzamido, 4-t-butylbenzamido, 4-vinylbenzamido, 2-trifluoromethylbenzamido, 3-trifluoromethylbenzamido, 4-trifluoromethylbenzamido, 2-fluoro-4-trifluoromethylbenzamido, 2-methoxybenzamido, 3-methoxybenzamido, 4-methoxybenzamido, 4-butoxybenzamido, 4-phenylphenylcarboxamido, 4-benzylcarboxamido, 4-phenoxymethylcarboxamido, 2-fluorobenzylamino, benzyloxy, 2-fluorobenzyloxy, 2-hydroxy-2-phenylethyl, 2-fluorophenylcarbamoyl, 4-(1-(2-(2-methoxycarbonylethanesulfonylamino)ethyl)phenyl, 4-(1-(2-(10-camphorsulfonylamino)ethyl)phenyl, 4-(1-(2-(benzylsulfonylamino)ethyl)phenyl, 4-(2-phenylacetamido) ethyl)phenyl, 4-(methanesulfonylaminoethanoyl)phenyl, 4-(N-t-butoxycarbonyl)methanesulfonylaminoethanoyl) phenyl, 2-thienylcarboxamido, 2-furylcarboxamido, 3-(5-methylisoxazolyl)carboxamido, 5-isoxazolylcarboxamido, 2-benzothienylcarboxamido, 4-(5-methyl-3-phenylisoxazolyl)carboxamido, 4-pyridylcarboxamido, 2-(5-nitrofuryl)carboxamido, 2-pyridylcarboxamido, 6-chlord-2-pyridylcarboxamido, 2-thienylsulfonamido, 2-thienylmethylamino, 3-thienylmethylamino, 2-furylmethylamino, 3-furylmethylamino, 3-acetylureido and 2-(2-thienyl)ethylureido.

Examples of particular values for $R^{21}$ are hydrogen and chlorine. $R^{21}$ is preferably ortho to $R^{20}$.

Examples of particular values for $R^1$ are 2-naphthyl, 4-bromophenyl, 4-cyanophenyl, 4-benzamidophenyl, 4-methylphenyl, 4-isopropylphenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl) phenyl, 4-(2-furyl)phenyl, 4-(3-furyl)phenyl, 4-(2-thienyl) phenyl, 4-(3-thienyl)phenyl, 4-(pyrrolidin-1-yl)phenyl, 4-(piperidin-1-yl)phenyl, 3-chloro-4-piperidin-1-ylphenyl, 4-benzyloxyphenyl, 4-(2-fluorophenyl)phenyl, 4-(3-fluorophenyl)phenyl, 4-(2-formylphenyl)phenyl, 4-(3-formylphenyl)phenyl, 4-(4-formylphenyl)phenyl, 4-(4-methylphenyl)phenyl, 4-(4-hydroxphenyl)phenyl, 4-(2-methoxyphenyl)phenyl and 4-(4-methoxyphenyl)phenyl.

The compounds of formula I may be prepared as described below. The reagents and starting material are readily available to one of ordinary skill in the art, for example see International Patent Application Publication WO 98/33496. Thus, the compounds of formula I may be prepared by:

(a) reacting a compound of formula

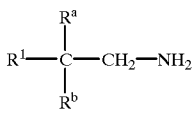

II with a compound of formula

III in which $Z^1$ represents a leaving atom or group; or (b) for a compound of formula I in which $R^a$ and $R^b$ together represent =O, reacting a compound of formula

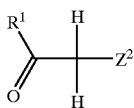

in which $Z^2$ represents a leaving atom or group, with a compound of formula $$HNR^xSO_2R^2 \qquad V$$

in which $R^x$ represents a hydrogen atom or an amine protecting group; followed where necessary and/or desired by removing any amine protecting group and forming a pharmaceutically acceptable salt.

In process step (a), the leaving atom or group represented by $Z^1$ may be, for example, a halogen atom such as a chlorine or bromine atom. The reaction is conveniently performed in the presence of a base, for example an alkali metal hydroxide such as sodium hydroxide, an alkali metal carbonate such as potassium carbonate, a tertiary amine such as triethylamine or 1,8-diazabicyclo[5.4.0]undec-7-ene. Suitable solvents include halogenated hydrocarbons such as dichloromethane. The reaction is conveniently performed at a temperature in the range of from −20 to 100° C., preferably from −5 to 50° C.

In process step (b), the amine protecting group represented by $R^x$ may be a conventional amine protecting group. The protection of amine groups is generally described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of amine protecting groups include acyl groups, such as groups of formula $R^yCO$ in which $R^y$ represents (1–6C) alkyl, (3–10C) cycloalkyl, phenyl(1–6C) alkyl, phenyl, (1–6C) alkoxy, phenyl(1–6C)alkoxy, or a (3–10C) cycloalkoxy, wherein a phenyl group may optionally be substituted by one or two substituents independently selected from amino, hydroxy, nitro, halogeno, (1–6C) alkyl, (1–6C) alkoxy, carboxy, (1–6C) alkoxycarbonyl, carbamoyl, (1–6C) alkanoylamino, (1–6C) alkylsulphonylamino, phenylsulphonylamino, toluenesulphonylamino, and (1–6C) fluoroalkyl. An example of a preferred amine protecting group is t-butoxycarbonyl. It may be removed by hydrolysis, for example using trifluoroacetic acid.

The leaving atom or group represented by $Z^2$ may be, for example, a halogen atom such as a chlorine or bromine atom. The reaction is conveniently performed in the presence of a base, for example an alkali metal hydroxide such as sodium hydroxide, an alkali metal carbonate such as potassium carbonate, a tertiary amine such as triethylamine or 1,8-diazabicyclo[5.4.0]undec-7-ene. Suitable solvents include halogenated hydrocarbons such as dichloromethane, nitriles, such as acetonitrile and ethers such as tetrahydrofuran. The reaction is conveniently performed at a temperature in the range of from −20 to 100° C., preferably from −5 to 50° C.

The compounds of formula I in which $R^1$ represents a 4-bromophenyl group may conveniently be converted into other compounds of formula I in which R represents another 4-substituted phenyl group by reaction with an appropriate boronic acid derivative, for example, 3-thiopheneboronic acid. The reaction is conveniently performed in the presence of a tetrakis (triarylphosphine)palladium(0) catalyst, such as tetrakis (triphenylphosphine)palladium(0) and a base such as potassium carbonate. Convenient solvents for the reaction include aromatic hydrocarbons, such as toluene, and ethers, such as dioxane. The temperature at which the reaction is conducted is conveniently in the range of from 0 to 150° C., preferably 75 to 120° C. Bis aromatic intermediates useful in the preparation of compounds of formula I may be prepared by reacting a bromoaromatic or bromoheteroaromatic compound with an aromatic or heteroaromatic boronic acid in an analogous manner.

The boronic acid derivative used as a starting material may be prepared by reacting a trialkyl borate, such as triisopropyl borate with an appropriate organolithium compound at reduced temperature. For example, 2-fluorobenzeneboronic acid may be prepared by reacting 2-fluorobromobenzene with butyllithium in tetrahydrofuran at about −78° C. to afford 2-fluorophenyl lithium, and then reacting this organolithium compound with triisopropyl borate.

Alternatively, the compounds of formula I in which $R^1$ represents a 4-bromophenyl group may be converted to a 4-(trimethylstannyl)phenyl or 4-(tri-n-butylstannyl)phenyl group by treatment of the corresponding bromide with a palladium(0) catalyst, such as tetrakis(triphenylphosphine) palladium(0) and hexaalkyldistannane, where the alkyl group is methyl or n-butyl, in an aprotic solvent such as toluene in the presence of a tertiary amine base such as triethylamine, at temperatures ranging from 80 to 140° C., preferably from 90 to 110° C.

The compounds of formula I in which $R^1$ represents a 4-(tri-n-butylstannyl)phenyl group may then be reacted with an aryl- or heteroarylbromide, such as 2-bromothiophene-5-carboxaldehyde, in the presence of a palladium(0) catalyst, such as tetrakis(triphenylphosphine)palladium(0), or a palladium(II) catalyst, such as bis(triphenylphosphine) palladium(II) dichloride, in an aprotic solvent, such as dioxane, at temperatures ranging from 80 to 140° C., preferably from 90 to 110° C., to afford the corresponding 4-(aryl)phenyl or 4-(heteroaryl)phenyl substituted compound.

The compounds of formula I in which $R^1$ represents a 4-bromophenyl group may be converted into other compounds of formula I in which $R^1$ represents a 4-substituted alkyl- or cycloalkylphenyl group, such as 4-cyclopentylphenyl by treatment of the corresponding bromide with an appropriate alkyl- or cycloalkyl Grignard reagent, such as cyclopentylmagnesium bromide, in the presence of a palladium(II) catalyst, such as [1,1'-bis (diphenylphosphino)ferrocene]dichloropalladium(II) ($PdCl_2$(dppf)), in an aprotic solvent, such as diethyl ether at temperatures ranging from −78° C. to 25° C.

The compounds of formula I in which $R^1$ represents a 4-bromophenyl group may be converted into a 4-substituted carboxyaldehydephenyl(formylphenyl) group by reaction of the corresponding bromide with the carbon monoxide gas which is bubbled into the reaction under atmospheric pressure in the presence of a palladium(II) catalyst, such as bis(triphenylphosphine)palladium(II) dichloride and sodium formate in an aprotic solvent, such as dimethylformamide at temperatures ranging from 70 to 110° C., preferably at 90° C.

The compounds of formula I in which $R^1$ represents a 4-hydroxyphenyl group may be converted into other compounds of formula I in which $R^1$ represents an alkoxy group by treatment of the corresponding hydroxyphenyl group with an appropriate alkylhalide such as benzylbromide in the presence of sodium hydride in an aprotic solvent such as dimethylformamide at temperatures ranging from 25 to 100° C., preferably from 50 to 90° C. The compounds of formula I in which $R^a$ and $R^b$ together represent =O may be converted into a compound of formula I in which one of $R^a$ and $R^b$ represents $OR^c$ and the other represents hydrogen by reduction, for example using lithium aluminium hydride or sodium borohydride, to afford a compound of formula I in which one of $R^a$ and $R^b$ represents OH, followed if desired by alkylation, for example by reaction with a (1–4C)alkyl halide in the presence of a base to afford a compound of formula I in which $R^a$ represents (1–4C)alkoxy.

The compounds of formula I in which $R^a$ and $R^b$ together represent =O may be converted into a compound of formula I in which $R^a$ and $R^b$ together represent =$CH_2$ by a Wittig reaction.

The compounds of formula I in which $R^a$ and $R^b$ together represent =O may be converted into a compound of formula I in which $R^a$ and $R^b$ each represents fluorine by reaction with a fluorinating agent such as diethylaminosulfur trifluoride or dimethylaminosulfur trifluoride, according to the method described in *J. Org. Chem*, 50, 1599, 1985 and *Tet. Lett.*, 34(31), 4917, 1993. The reaction is conveniently performed in a solvent such as dichloromethane or tetrahydrofuran at a temperature in the range of from 0 to 50° C. Alternative fluorinating agents are hydrogen fluoride in trifluoroacetic acid and $CF_2Br_2$ with zinc dust (*J. Chem. Soc. Perk. Trans.* 1, 3, 335, 1993). Alternatively, the compound of formula I may be converted to a dithiolane by reaction with $H_2SCH_2CH_2SH$, followed by reaction with $BF_3$-acetic acid complex (*J. Org. Chem.*, 51, 3508, 1986).

The compounds of formula II are known or may be prepared by conventional methods, for example by reducing a corresponding amide or nitrile using a borane.

Alternatively, the compounds of formula II in which $R^a$ represents $CF_3$ may be prepared by reducing a compound of formula

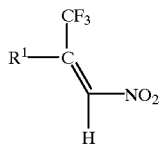

VI for example by catalytic hydrogenation using a Group VIII metal catalyst, such as palladium on charcoal.

The compounds of formula VI may be prepared by reacting a compound of formula

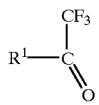

VII with nitromethane. The reaction is conveniently performed in the presence of a base, such as diethylenediamine in a solvent, such as toluene, and using a Dean and Stark trap to remove water formed during the reaction.

The compounds of formula IV are known or may be prepared by conventional methods. For example a compound of formula IV in which $Z^1$ represents a bromine atom may be prepared from the corresponding ketone of formula

VIII by bromination using an electrophilic brominating agent, such as bromine or N-bromosuccinimide. Convenient solvents include acetic acid. Alternatively, they may be prepared by treating the corresponding ketone of formula VIII with a strong base, such as lithium diisopropyl amide or lithium bis(trimethylsilyl)amide in a solvent such as tetrahydrofuran, followed by a brominating agent, such as bromine or N-bromosuccinimide.

More specifically, compounds of formula Ia and formula Ib can be prepared following generally the procedure described in Scheme I. The reagents and starting materials are readily available to one of ordinary skill in the art. Unless otherwise indicated, the substituents are defined as above.

Scheme 1

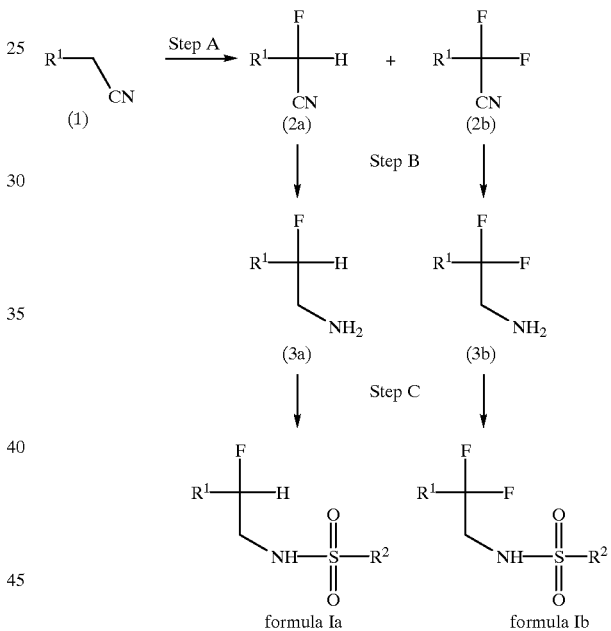

In Scheme I, step A the nitrile of structure (1) is fluorinated to provide the monofluoro compound (2a) and the difluoro compound (2b). For example, the nitrile (1) is dissolved in a suitable organic solvent, such as dry tetrahydrofuran and about 2.2 equivalents of N-fluorobenzene sulfonamide is added to the solution under an atmosphere of nitrogen. The solution is cooled to about −78° C. with stirring and treated dropwise with about 2.2 equivalents of lithium-bis-(trimethylsilyl)amide. The reaction is then allowed to warm to room temperature and then stirred for about 8 to 16 hours. The reaction mixture is then diluted with water and extracted with a suitable organic solvent, such as ethyl acetate. The organic extracts are washed with water, dried over anhydrous sodium sulfate, filtered and concentrated to provide a crude mixture of compounds (2a) and (2b). These are separated and purified by techniques well known in the art, such as flash or radial (Chromatotron, Harrison Research Inc., Palo Alto, Calif.) chromatography on silica gel. For example, the crude material is purified by radial chromaography on a 4000 micron silica gel rotor eluting with a suitable eluent, such as ethyl acetate/hexane to provide separately the purified monofluoro compound (2a) and the difluoro compound (2b).

In Scheme I, step B each compound (2a) and (2b) can be reduced under standard conditions well known in the art to provide the amino derivatives (3a) and (3b). For example, either compound (3a) or compound (3b) is dissolved in a suitable organic solvent, such as dry tetrahydrofuran at room temperature under an atmosphere of nitrogen wit stirring. The solution is then treated with about 1.3 equivalents of $BH_3$-THF complex and stirred for about 4 to 24 hours. The reaction mixture is then treated with an excess of a mixture of THF/methanol (1:1) followed by dropwise addition of excess 5.0 N sodium hydroxide. The reaction mixture is then stirred under reflux for about 3 to 6 hours and then cooled to room temperature. The reaction mixture is then diluted with a suitable organic solvent, such as ethyl acetate. The organic layer is separated, washed with water, dried over anhydrous sodium sulfate, filtered and concentrated under vacuum to provide the crude material. The crude material is purified by standard techniques well known in the art such as flash or radial chromatography on silica gel with a suitable eluent, such as methanol/methylene chloride to provide the purified compounds (3a) or (3b).

In Scheme I, step C the compounds (3a) or (3b) are converted to the corresponding sulfonamides of formula (Ia) or formula (Ib) under conditions well known in the art. For example, either compound (3a) or (3b) is dissolved in a suitable organic solvent, such as dry methylene chloride under an atmosphere of nitrogen. To this solution is added about 2.1 equivalents of DBU. The solution is then cooled to about 0° C. and treated dropwise with about 1.1 equivalents of a compound of formula $ClSO_2R^2$. The reaction mixture is then allowed to warm to room temperature and stirred for about 8 to 16 hours. It is then poured into water and the organic layer is separated. The organic layer is then washed with water, dried over anhydrous sodium sulfate, filtered and concentrated under vacuum to provide the crude product of formula (Ia) or formula (Ib). This crude material can then be purified by standard techniques well known in the art, such as flash or radial chromatography bn silica gel with a suitable eluent, such as hexane/ethyl acetate to provide the purified compounds of formula (Ia) or formula (Ib).

The ability of compounds of formula I to potentiate glutamate receptor-mediated response may be determined using fluorescent calcium indicator dyes (Molecular Probes, Eugene, Oreg., Fluo-3) and by measuring glutamate-evoked efflux of calcium into GluR4 transfected HEK293 cells, as described in more detail below.

In one test, 96 well plates containing confluent monolayers of HEK cells stably expressing human GluR4B (obtained as described in European Patent Application Publication Number EP-A1-583917) are prepared. The tissue culture medium in the wells is then discarded, and the wells are each washed once with 200 µl of buffer (glucose, 10 mM, sodium chloride, 138 mM, magnesium chloride, 1 mM, potassium chloride, 5 mM, calcium chloride, 5 mM, N-[2-hydroxyethyl]-piperazine-N-[2-ethanesulfonic acid], 10 mM, to pH 7.1 to 7.3). The plates are then incubated for 60 minutes in the dark with 20 µM Fluo3-AM dye (obtained from Molecular Probes Inc, Eugene, Oreg.) in buffer in each well. After the incubation, each well is washed once with 100 µl buffer, 200 µl of buffer is added and the plates are incubated for 30 minutes.

Solutions for use in the test are also prepared as follows. 30 µM, 10 µM, 3 µM and 1 µM dilutions of test compound are prepared using buffer from a 10 mM solution of test compound in DMSO. 100 µM cyclothiazide solution is prepared by adding 3 µl of 100 mM cyclothiazide to 3 ml of buffer. Control buffer solution is prepared by adding, 1.5 µl DMSO to 498.5 µl of buffer.

Each test is then performed as follows. 200 µl of control buffer in each well is discarded and replaced with 45 µl of control buffer solution. A baseline fluorescent measurement is taken using a FLUOROSKAN II fluorimeter (Obtained from Labsystems, Needham Heights, Mass., USA, a Division of Life Sciences International Plc). The buffer is then removed and replaced with 45 µl of buffer and 45 µl of test compound in buffer in appropriate wells. A second fluorescent reading is taken after 5 minutes incubation. 15 µl of 400 µM glutamate solution is then added to each well (final glutamate concentration 100 µM), and a third reading is taken. The activities of test compounds and cyclothiazide solutions are determined by subtracting the second from the third reading (fluorescence due to addition of glutamate in the presence or absence of test compound or cyclothiazide) and are expressed relative to enhance fluorescence produced by 100 µM cyclothiazide.

In another test, HEK293 cells stably expressing human GluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm $kg^{-1}$. The intracellular recording solution contains (in mM): 140 CsCl, 1 $MgCl_2$, 10 HEPES, (N-[2-hydroxyethyl]piperazine-$N^1$-[2-ethanesulfonic acid]) 10 EGTA (ethylene-bis (oxyethylenenitrilo)tetraacetic acid), pH=7.2 with CsOH, 295 mOsm $kg^{-1}$. With these solutions, recording pipettes have a resistance of 2–3 MΩ. Using the whole-cell voltage clamp technique (Hamill et al. (1981) Pflügers Arch., 391: 85–100), cells are voltage-clamped at −60 mV and control current responses to 1 mM glutamate are evoked. Responses to 1 mM glutamate are then determined in the presence of test compound. Compounds are deemed active in this test if, at a test concentration of 10 µM, they produce a greater than 30% increase in the value of the current evoked by 1 mM glutamate.

In order to determine the potency of test compounds, the concentration of the test compound, both in the bathing solution and co-applied with glutamate, is increased in half log units until the maximum effect was seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 µM cyclothiazide is determined by its inclusion in both the bathing solution and the glutamate-containing solution. In this manner, the efficacy of the test compound relative to that of cyclothiazide can be determined.

According to another aspect, the present invention provides a pharmaceutical composition, which comprises a compound of formula I or a pharmaceutically acceptable salt thereof as defined hereinabove and a pharmaceutically acceptable diluent or carrier.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

As used herein the term "patient" refers to a mammal, such as a mouse, guinea pig, rat, dog or human. It is understood that the preferred patient is a human.

As used herein the term "effective amount" refers to the amount or dose of the compound which provides the desired effect in the patient under diagnosis or treatment.

The compositions are preferably formulated in a unit dosage form, each dosage containing from about 1 mg to about 500 mg, more preferably about 5 mg to about 300 mg (for example 25 mg) of the active ingredient. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient. The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

The above ingredients are mixed and filled into hard gelatin capsules in 460 mg quantities.

Formulation 2

Tablets each containing 60 mg of active ingredient are made as follows:

|  |  |
| --- | --- |
| Active Ingredient | 60 mg |
| Starch | 45 mg |
| Microcrystalline cellulose | 35 mg |
| Polyvinylpyrrolidone | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate, and talc, previously passed through a No. 60 mesh U.S. sieve, are then added to the granules which, after mixing, are compressed on a tablet machine to yield tablets each weighing 150 mg.

The particular dose of compound administered according to this invention will of course be determined by the particular circumstances surrounding the case, including the compound administered, the route of administration, the particular condition being treated, and similar considerations. The compounds can be administered by a variety of routes including oral, rectal, transdermal, subcutaneous, intravenous, intramuscular, or intranasal routes. Alternatively, the compound may be administered by continuous infusion. A typical daily dose will contain from about 0.01 mg/kg to about 100 mg/kg of the active compound of this invention. Preferably, daily doses will be about 0.05 mg/kg to about 50 mg/kg, more preferably from about 0.1 mg/kg to about 25 mg/kg.

The following examples and preparations represent typical syntheses of the compounds of the present invention. These examples are illustrative only and are not intended to limit the invention in any way. The reagents and starting materials are readily available to one of ordinary skill in the art. As used herein, the following terms have the meanings indicated: "eq" refers to equivalents; "g" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "°C." refers to degrees Celsius; "HPLC" refers to high performance liquid chromatography; "THF" refers to tetrahydrofuran; "DMF" refers to N,N-dimethylformamide; "DMSO" refers to methyl sulfoxide; "LDA" refers to lithium diisopropylamide; "EtOAc" refers to ethyl acetate; "aq" refers to aqueous; "iPrOAc" refers to isopropyl acetate; "DBU" refers to 1,8-diazabicyclo[5.4.0]undec-7-ene; "MeOH" refers to methanol; and "RT" refers to room temperature.

Preparation 1

Preparation of N-[2-(4-Bromophenyl)-2-hydroxyethyl]-N-(t-butoxycarbonyl) Methanesulfonamide.

A. N-(t-butoxycarbonyl)methanesulfonamide: To a solution of 15.0 g (157.7 mmol) of methanesulfonamide, 17.6 g (173.5 mmol) of triethylamine and 1.9 g (15.8 mmol) of 4-dimethylaminopyridine in 200 mL of dichloromethane was added of 37.9 g (173.5 mmol) of di-t-butyldicarbonate in 200 mL of dichloromethane over ten minutes. The mixture was stirred at ambient temperature for 2.25 hours and concentrated in vacuo. The residue was dissolved in 250 mL of ethyl acetate and washed once with 200 mL of 1 N hydrochloric acid, once with 100 mL of water and once with 100 mL of saturated aqueous sodium chloride. The organic layer was dried (MgSO$_4$), filtered and concentrated in vacuo. The residue was suspended in 100 mL of hexane, filtered and dried in vacuo to afford 26.1 g (85%) of the title compound.

Analysis calculated for $C_7H_{13}NO_4S$: % C, 36.91; % H, 6.71; % N, 7.17. Found: % C, 36.97; % H, 6.79; % N, 7.04. Mass Spectrum: M+1=196.

B. N-(4-bromophenyl)carbonylmethyl-N-t-butoxycarbonyl methanesulfonamide: A solution of 1.0 g (5.1 mmol) of material from Step A, 1.4 g (5. lmmol) of 2,4'-dibromoacetophenone and 0.8 g (5.6 mmol) of potassium carbonate in 25 mL of acetonitrile was stirred at ambient temperature for two hours. The mixture was diluted with 25 mL of ethyl acetate and washed once with 15 mL of water. The organic layer was separated and the aqueous layer was extracted three times with 10 mL each of ethyl acetate. The combined organics were dried (MgSO$_4$), filtered and concentrated in vacuo. Chromatography (50 g of silica gel, 20% ethyl acetate/hexane) of the residue afforded 1.5 g (76%) of the title compound.

Analysis calculated for $C_{14}H_{17}NBrO_5S$: % C, 42.87; % H, 4.63; % N, 3.57. Found: % C, 43.11; % H, 4.66; % N, 3.37. Mass Spectrum: M−1=391.

C. N-[2-(4-Bromophenyl)2-hydroxyethyl]-N-(t-butoxycarbonyl) methanesulfonamide: To a solution of 2.6 g (6.7 mmol) of material from Step B in 25 mL of ethanol was added 0.3 g (6.7 mmol) of sodium borohydride and the mixture was stirred for 16 hours. The mixture was concentrated in vacuo and the residue was partitioned between 25 mL of ethyl acetate and 25 mL of water. The organic layer was separated and the aqueous layer was extracted three times with 10 mL each of ethyl acetate. The combined organics were dried (MgSO$_4$), filtered and concentrated in vacuo to afford 2.6 g (98%) of the title compound.

Analysis calculated for $C_{14}H_{19}NBrO_5S$: % C, 42.65; % H, 5.11; % N, 3.55. Found: % C, 42.60; % H, 5.08; % N, 3.46. Mass Spectrum: M=394.

Preparation 2
Preparation of 2-(4-Bromophenyl)-3,3,3-trifluoronitropropene.

A stirred solution of 4'-bromo-2,2,2-trifluoroacetophenone (0.392 g, 2.00 mmol) and CH$_3$NO$_2$ (0.488 g, 8.0 mmol) in dry toluene (70 mL) containing N,N-diethylenediamine (30 mmol) is heated at reflux with a Dean and Stark trap until complete removal of H$_2$O. The cooled solution is washed with 5% aqueous HCl, dried over MgSO$_4$, filtered, evaporated in vacuo and the resulting residue when purified by chromatography gives the title compound.

Preparation 3
Preparation of 2-(4-(4-Methoxyphenyl)phenyl)-3,3,3-trifluoronitropropene.

To a stirred solution of the product of Preparation 2 (0.296 g, 1.00 mmol) in ethylene glycol dimethyl ether (DME, 25 mL) is added tetrakis triphenylphosphine palladium (0) (0.046 g, 0.04 mmol), p-methoxyphenylboronic acid (0.167 g, 1.1 mmol), 2M Na$_2$CO$_3$ (1.2 mL, 2.4 mmol), propanol (1.0 mL) and the resulting mixture is heated and stirred at reflux for 6 h. The reaction mixture is then diluted with ethyl acetate (50 mL) and filtered. Evaporation of the filtrate in vacuo followed by chromatography gives the title compound.

Preparation 4

Preparation of 2-(4-(4-Methoxyphenyl)phenyl)-3,3,3-trifluoropropylamine Hydrochloride.

The product of Preparation 3 (0.323 g, 1.0 mmol) is hydrogenated in ethanol (50 mL) containing 3.0 mL of 1N HCl using 0.100 g 5% Pd on carbon at 60 psi until H$_2$ uptake is complete. The catalyst is removed by filtration and the amine is isolated as the hydrochloride.

Preparation 5

Preparation of:

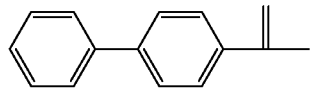

Into a flame dried 250 mL 3n flask fitted with a stirrer, thermometer, and condenser was added 32 mL N-Butyl-Li (32.0 mmol) dropwise to 10.7 g of Methyl Triphenylphosphonium Bromide in 250 mL of dry THF while stirring at 0° C. under a nitrogen atmosphere. This light yellow solution was allowed to warm to room temperature and 4.1 g of 4-Acetyl-biphenyl in 20 mL of dry THF was added dropwise. The reaction was then stirred overnight at room temperature. In the morning, the reaction was diluted with 200 mL each of H$_2$O and Ethyl Acetate and the layers were separated. The organic layer was washed two times with H$_2$O, dried over Na$_2$SO$_4$, filtered and concentrated under reduced vacuum to yield 3.8 g of the olefin title compound as a light tan solid (Yield=93%). FDMS 194 (M*).

Preparation 6

Preparation of:

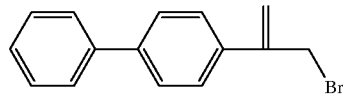

Into a 250 mL 3 necked flask fitted with a stirrer, thermometer, and condenser, was added the olefin prepared in Preparation 5 (2.0 g, 10.0 mmol), N-bromosuccinamide (1.4 g, 8.0 mmol) and benzoyl peroxide (catalytic amount) in 125 mL methylene chloride. The reaction was heated at 160° C. with vigorous reflux and then cooled after 10 minutes of reflux, stirring under a nitrogen atmosphere. After cooling to room temperature, the mixture was filtered and the resulting filtrate was concentrated under reduced vacuum to yield a yellow solid. This material was purified via silica gel chromatography employing the chromatotron and using a 2000 micron rotor while eluting with Hexane as a solvent to yield 310 mg of the bromo-olefin title compound as a white solid (Yield=11%). Ion spray M.S. 274 (M*+1).

Analysis calculated for $C_{15}H_{14}Br$:

| Theory: | C, 65.95 | H, 4.80 |
| Found: | C, 66.52 | H, 5.05 |

Preparation 7

Preparation of:

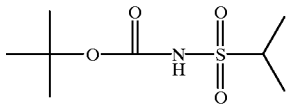

Into a 250 mL 3 necked flask fitted with a stirrer and thermometer 1.55 g of Di-tertbutyl- dicarbonate in 25 mL of CH$_2$Cl$_2$ was added dropwise to 814 m of:

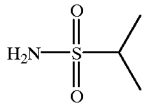

717 mg of Triethylamine, and 81 mg of Dimethylamino Pyridine in 100 mL CH$_2$C$_{12}$ while stirring at room temperature under a nitrogen atmosphere. The reaction was then stirred overnight at this temperature. In the morning, the solution was concentrated under reduced vacuum. The resulting oil was purified via silica gel chromatography employing the chromatotron and using a 4000 micron rotor while eluting with a gradient solvent of Hexane/Ethyl Acetate 9:1 to Hexane/Ethyl Acetate 1:1 to yield 399 mg of the N-protected isopropylsulfonamide title compound as a clear oil (Yield=28%). Ion spray M.S. 222 (M*−1).

Analysis was calculated for C$_8$H$_{17}$NO$_4$S:

| Theory: | C, 43.05 | H, 7.62 | N, 6.28 |
|---|---|---|---|
| Found: | C, 44.85 | H, 7.79 | N, 5.89 |

Preparation 8

Preparation of:

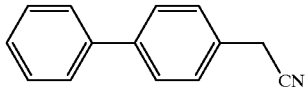

Into a 250 mL single neck flask was placed 4-bromophenylacetonitrile (4.6 g, 25 mmol), phenylboronic acid (4.6 g, 3.8 mmol), potassium carbonate (5.2 g, 3.8 mmol) and tetrakis(triphenylphosphine)Pd(0) (1.46 g, 1.3 mmol in dioxane/water (100 mL, 3:1) and the mixture was heated at 100° C. under stirring for 18 hours. The reaction was cooled to room temperature and poured into H$_2$O. The desired product was extracted with ethyl acetate and the organic layer was washed twice with H$_2$O, dried over Na$_2$SO$_4$, filtered and concentrated under reduced vacuum. The resulting semi-solid was purified via silica gel chromatography employing the Prep. LC 2000 and eluting with a solvent of Hexane/ethyl acetate 4:1 to yield 4.2 g the nitrile title compound as a pale yellow solid. (Yield=88%). FDMS 193 (M*).

Analysis for C$_{14}$H$_{11}$N

| Theory: | C, 87.10 | H, 5.74 | N, 7.25 |
|---|---|---|---|
| Found: | C, 87.58 | H, 5.92 | N, 7.25 |

Preparation 9

Preparation of:

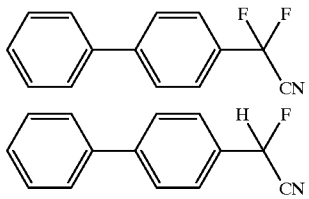

Into a 500 mL 3 necked flask fitted with a stirrer and thermometer, 25 mL of Lithium-bis-(trimethylsilyl)amide (25 mL, 25 mmol, 1M solution) was added dropwise to 2.22 g of the nitrile prepared in preparation 8 and 7.90 g of N-fluorobenzene sulfonamide in 200 mL THF while stirring at −78° C. under nitrogen. The reaction was allowed to warm to room temperature, and stirred overnight at this temperature. In the morning, the reaction was diluted with H$_2$O and desired product was extracted with ethyl acetate. The organic layer was backwashed with H$_2$O, dried over Na$_2$SO$_4$, filtered and concentrated under reduced vacuum. This material was purified via silica gel chromatography employing the chromatotron (Harrison Research Inc, Palo Alto, Calif.) using a 2000 micron rotor and eluting with a solvent of Hexane/ethyl acetate 9:1 to yield 836 mg of the difluoronitrile title compound as a viscous oil. FDMS 229 (M*).

Analysis for C$_{14}$H$_9$NF$_2$

| Theory: | C, 73.36 | H, 3.96 | N, 6.11 |
|---|---|---|---|
| Found: | C, 73.18 | H, 4.21 | N, 5.99 |

210 mgs. of the monofluoronitrile title compound was isolated as a solid. FDMS 211 (M*).

Preparation 10

Preparation of:

Into a 100 mL 3 necked flask fitted with a stirrer, thermometer, and condensor was added syringe wise 4.5 mL BH$_3$-THF complex (4.5 mL, 4.5 mmol, 1 M solution) to 798 mg. of the difluoronitrile prepared in preparation 9 in 15 mL THF while stirring at room temperature under a nitrogen atmosphere. The solution was then stirred overnight at this temperature. In the morning, 5 mL of THF/MeOH 1:1 was added dropwise at room temperature followed by the dropwise addition of 2 mL 5.0 N NaOH. (vigorous foaming occurred). The reaction was then stirred under reflux for 5 hours. The solution was allowed to cool to room temperature and diluted with 200 mL ethyl acetate. The organic layer was separated and washed once with H$_2$O, dried over Na$_2$SO$_4$, filtered and concentrated under reduced vacuum to yield a viscous oil. This oil was then purified via silica gel chromatography employing the chromatotron and using a 4000 micron rotor and eluting with a solvent of $CH_2Cl_2$/MeOH 99:1 to yield 710 mg. of the difluoroamino title compound as a white solid. (Yield=87%). FDMS 233 (M*).

Analysis for $C_{14}H_{13}NF_2$:

| | | | |
|---|---|---|---|
| Theory: | C, 72.09 | H, 5.62 | N, 6.00 |
| Found: | C, 74.32 | H, 5.87 | N, 6.03 |

Preparation 11

Preparation of:

Into a 50 mL 3n flask fitted with a stirrer, thermometer, and condenser was added syringe wise 2.0 mL $BH_3$-THF complex (2.0 mL, 2.00 mmol, 1M solution) to 208 mg of the monofluoronitrile prepared in preparation 9, in 10 mL THF while stirring at room temperature under a nitrogen atmosphere. The solution was then stirred overnight at this temperature. In the morning, 5 mL of THF/MeOH 1:1 was added dropwise at room temperature followed by the dropwise addition of 2 mL 5.0 N NaOH. (vigorous foaming occurred). The reaction was then stirred under reflux for 5 hours. The solution was allowed to cool to room temperature and diluted with 10 mL ethyl acetate. The organic layer was separated and washed once with $H_2O$, dried over $Na_2SO_4$, filtered, and concentrated under reduced vacuum to yield a viscous oil. The material was purified via silica gel chromatography employing the chromatotron (Harrison Research Inc., Palo Alto, Calif.) and using a 2000 micron rotor and eluting with a solvent of $CH_2Cl_2$/MeOH 9:1 to yield 52 mg of the title compound as a white foam. (Yield= 25%). FDMS 215 (M*).

EXAMPLE 1

Preparation of N-2-(4-bromophenyl)-2-methoxyethyl Methanesulfonamide.

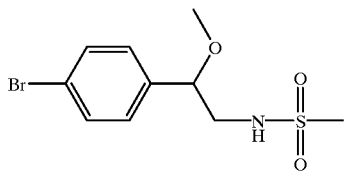

A. N-t-butoxycarbonyl-N-2-(4-bromophenyl)-2-methoxyethyl methanesulfonamide: To a solution of 1.0 g (2.5 mmol) of material from Preparation 1 in 8 mL of tetrahydrofuran was added 2.7 mL (2.7 mmol) of a 1.0 M solution of sodium bis(trimethylsilyl)amide in tetrahydrofuran. The mixture was stirred at ambient temperature for 10 minutes and 3.6 g (25.4 mmol) of iodomethane was added. The reaction mixture was heated to 70° C. for 16 hours, cooled to ambient temperature and diluted with 10 mL of water. The mixture was extracted three times with 10 mL each of diethyl ether. The combined organic portions were dried ($MgSO_4$), filtered and concentrated in vacuo. The residue was suspended in diethyl ether, filtered and dried to afford 0.4 g (39%) of the title compound.

B. To an ambient temperature solution of 0.4 g (0.9 mmol) of material from part A in 5 mL of dichloromethane was added 1.1 g (9.3 mmol) of trifluoroacetic acid and the mixture was stirred for 16 hours and concentrated in vacuo. Chromatogaphy (50 g silica gel, 35% ethyl acetate/hexane) of the residue afforded 0.2 g (75%) of the title compound.

Analysis calculated for $C_{10}H_{14}NO_3SBr$: % C, 38.97; % H, 4.58; % N, 4.54. Found: % C, 39.08; % H, 4.31; % N, 4.49. Field Desorption Mass Spectrum: M-1=307.

EXAMPLE 2

Preparation of N-2-[4-(4-Methoxyphenyl)phenyl]-3,3,3-trifluoropropyl 2-Propanesulfonamide.

To a stirred mixture of the product of Preparation 4 (1.0 mmol) in dichloromethane (20 mL) under $N_2$ at 0° C. is added 1,8-diazabicyclo[5.4.0]undec-7-ene (DBU, 3.0 mmol). The reaction mixture is stirred for 30 min., followed by the dropwise addition of isopropylsulfonyl chloride (1.2 mmol). The reaction mixture is then allowed to warm to ambient temperature and then heated at reflux until the reaction is complete by thin layer chromatography (TLC). 1N HCl (10 mL) is then added and the organic layer is separated. The aqueous layer is extracted with dichloromethane (25 mL). All the organic layers are combined, washed with saturated $NaHCO_3$ and brine, dried and evaporated. The residue is purified by chromatography to provide the title compound.

EXAMPLE 3

Preparation of N-2-[4-(4-Hydroxyphenyl)phenyl]-3,3,3-trifluoropropyl 2-Propanesulfonamide.

To a stirred solution of the product from Example 2 1.00 mmol in dichloromethane (20 mL) at 0° C. under $N_2$ is added 1.5 mmol of 1.0 M $BBr_3$ in dichloromethane. The resulting mixture is allowed to warm to ambient temperature and stirred overnight. The mixture is cooled to 0° C. and diluted with $H_2O$ (5.0 mL ). The dichloromethane layer is separated, dried, filtered and evaporated in vacuo. Chromatography on silica gel to provide the title compound.

EXAMPLE 4

Preparation of N-2-(4-(3-thienyl)phenyl)2-methoxyethyl Methanesulfonamide.

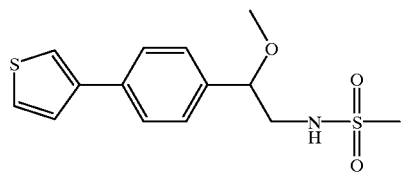

N-2-(4-Bromophenyl)-2-methoxyethyl methanesulfonamide (0.14 g, 0.45 mmol) and 3-thiopheneboronic acid (0.07 g, 0.55 mmol) were combined in a solution of dioxane (3 mL) and 2 M $Na_2CO_3$ (1 mL). Tetrakis-triphenylphosphine palladium (0.02 g, 0.02 mmol) was added and the reaction was heated at reflux for 6 hours then quenched with 1 M HCl. This solution was extracted with $CH_2C_{12}$, and the combined organics were washed with saturated $NaHCO_3$ and saturated NaCl, dried ($MgSO_4$) and concentrated to a brown oil. The crude material was purified by chromatography, eluting with 1:1 ethyl acetate/hexanes to yield 0.06 g (40%) of an off-white solid. $^1$HNMR (400 MHz, $CDCl_3$): δ 2.82 (3H, s), 2.94 (3H, s), 3.23 (1H, dd, J=14.2, 3.4 Hz), 3.43 (1H, dd, J=14.0, 8.0 Hz), 4.92 (1H, dd, J=8.8, 3.6 Hz), 7.35–7.64 (7H, m).

EXAMPLE 5
Preparation of Intermediate:

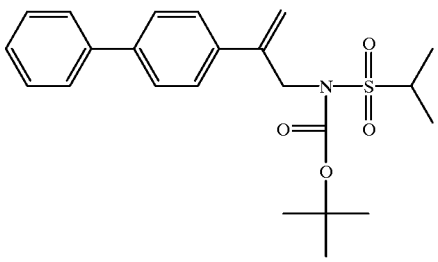

Into a 100 mL 3 necked flask fitted with a stirrer and thermometer, 310 mg of bromo-olefin (prepared in preparation 6) in 5 mL $CH_3CN$ was added dropwise to 253 mg of the N-protected-Isopropyl Sulfonamide (prepared in preparation 7) and 172 mg of $K_2CO_3$ in 45 mL $CH_3CN$ while stirring at room temperature under a nitrogen atmosphere. The white cloudy solution was then stirred over night at this temperature. In the morning, the mixture was diluted with 100 mL each of $H_2O$ and Ethyl Acetate and the layers were separated. The organic layer was washed twice with $H_2O$, dried over $Na_2SO_4$, filtered and concentrated under reduced vacuum to yield a tan oil. This crude material was purified via silica gel chromatography employing the chromatotron using a 4000 micron rotor and eluting with Hexane/Ethyl Acetate 9:1 to yield 38 mg of the intermediate title compound as a clear viscous oil (Yield=8%) FDMS 415.3 (M*).

Preparation of Final Title Compound:

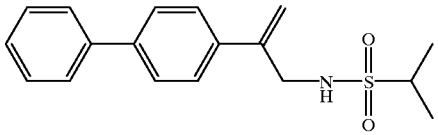

Into a 5 mL single neck flask fitted with a stirrer were placed the above prepared intermediate title compound (33 mg) and 1N HCl/ethyl acetate (1:1, 1 mL). Then the flask was sealed and the reaction was stirred over night at room temperature. In the morning, the solution was concentrated under reduced vacuum, taken into 20 mL Acetone and concentrated again to insure removal of the HCl. The resulting oil was purified via silica gel chromatography employing the chromatotron using a 2000 micron rotor and eluting with a solvent of Hexane/Ethyl Acetate 4:1 to yield 7.6 mgs. of final title compound as a clear viscous oil (Yield=13%).

Ion spray M.S. 316 (M*+1).

EXAMPLE 6
Preparation of:

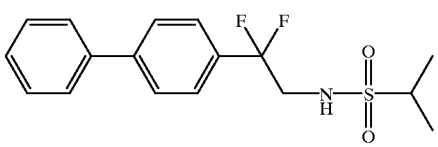

Into a 100 mL 3 necked flask fitted with a stirrer and thermometer, was added dropwise 485 mg of 2-Propanesulfonyl chloride to 710 mg of the difluoroamino compound (prepared in preparation 10) and 958 mg of DBU in 50 mL $CH_2Cl_2$ while stirring at 0° C. under nitrogen. Reaction was allowed to warm to room temperature and stirred overnight at this temperature. In the morning, the mixture was poured into $H_2O$ and the layers were separated. The organic layer was washed once with $H_2O$, dried over $Na_2SO_4$, filtered and concentrated under reduced vacuum. The crude material was separated and purified via silica gel chromatography employing the chromatotron using a 4000 micron rotor and eluting with a solvent of methylene chloride/methanol 9:1 to yield 502 mgs. of the title compound as a solid material. m.p. 119°–121° C. (Yield=50%).

FRMS 339 (M*). Analysis for $C_{17}H_{19}NO_2SF_2$:

| Theory: | C, 60.16 | H, 5.64 | N, 4.13 |
| Found: | C, 59.88 | H, 5.66 | N, 4.00 |

EXAMPLE 7

Preparation of:

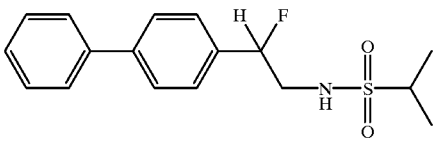

Into a 100 mL 3 necked flask fitted with a stirrer and thermometer, was added dropwise 43 mg of 2-Propanesulfonyl chloride to 52 mg of the monofluoroamino compound (prepared in preparation 11) and 91 mg of DBU in 25 mL $CH_2Cl_2$ while stirring at 0° C. under nitrogen. Reaction was allowed to warm to room temperature and stirred overnight at this temperature. In the morning, the mixture was poured into $H_2O$ and the layers were separated. The organic layer was washed once with $H_2O$, dried over $Na_2SO_4$, filtered and concentrated under reduced vacuum. The resulting crude material was separated and purified via silica gel chromatography employing the chromatotron using a 2000 micron rotor and eluting with a solvent of Hexane/ethyl acetate 9:1 to yield 26 mg of the title compound as a solid material. m.p. 89°–91° C. (Yield= 26%). Ion spray mass spectra 320 (M*–1).

Analysis for $C_{17}H_{20}NO_2SF$:

| Theory: | C, 63.53 | H, 6.27 | N, 4.36 |
| Found: | C, 62.90 | H, 6.46 | N, 4.30 |

The following Table I specifically illustrates additional preferred substituents for $R^1$ Table I.

TABLE I
R[1]
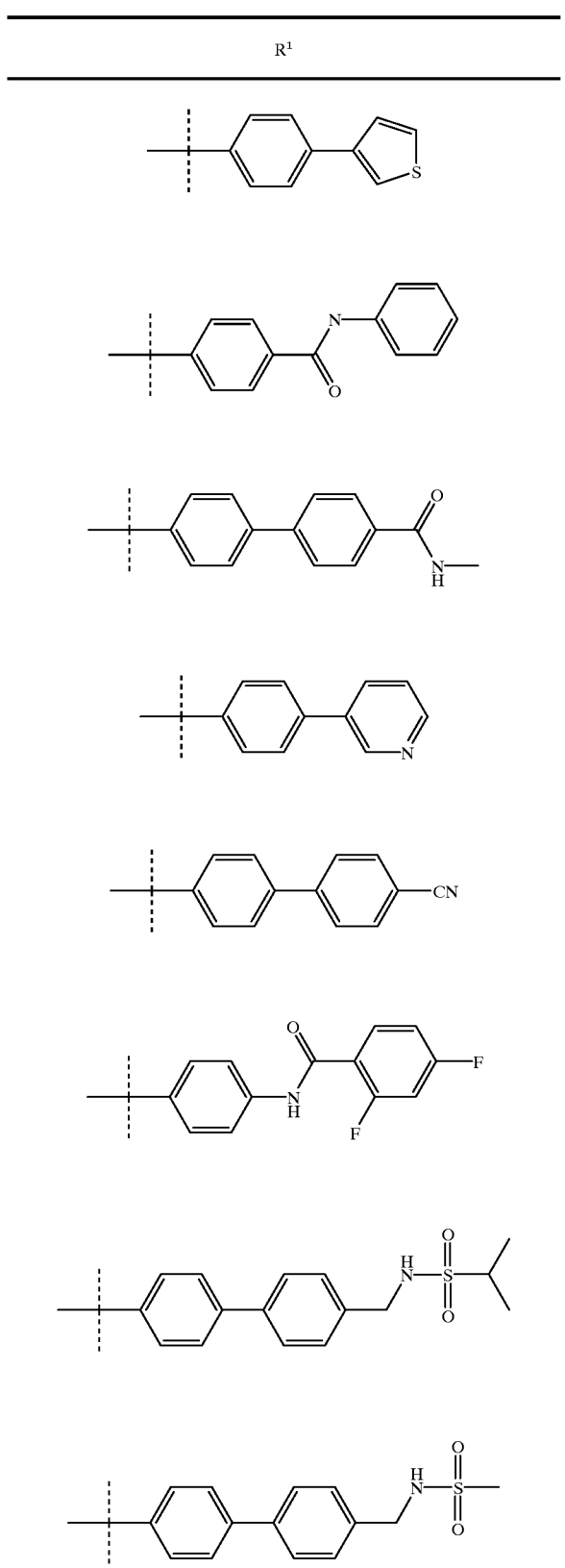
TABLE I-continued
R[1]
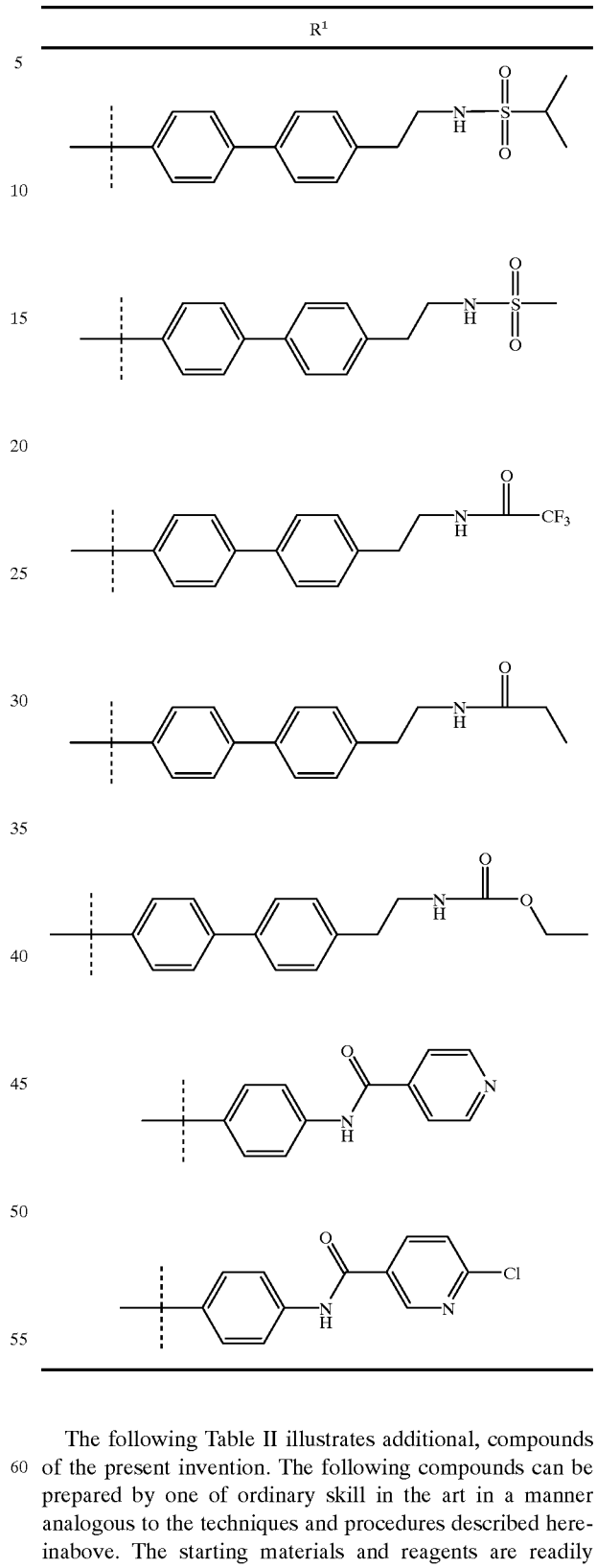
The following Table II illustrates additional, compounds of the present invention. The following compounds can be prepared by one of ordinary skill in the art in a manner analogous to the techniques and procedures described hereinabove. The starting materials and reagents are readily available to one of ordinary skill in the art.

TABLE II

| Example | Compound |
|---------|----------|
| 8 | |
| 9 | |
| 10 | |
| 11 | |
| 12 | |
| 13 | |
| 14 | |
| 15 | |
| 16 | |

TABLE II-continued

| Example | Compound |
|---------|----------|
| 17 | 4-(benzoylamino)-α-fluoro-N-(isopropylsulfonyl)benzeneethanesulfonamide analog (phenyl-C(O)NH-C6H4-CHF-CH2-NH-SO2-CH(CH3)2) |
| 18 | 3-pyridyl-C6H4-CF2-CH2-NH-SO2-CH(CH3)2 |
| 19 | 3-pyridyl-C6H4-CHF-CH2-NH-SO2-CH(CH3)2 |
| 20 | 2,4-difluorophenyl-C(O)NH-C6H4-CF2-CH2-NH-SO2-CH(CH3)2 |
| 21 | 2,4-difluorophenyl-C(O)NH-C6H4-CHF-CH2-NH-SO2-CH(CH3)2 |
| 22 | 4-pyridyl-C(O)NH-C6H4-CF2-CH2-NH-SO2-CH(CH3)2 |
| 23 | 6-chloro-3-pyridyl-C(O)NH-C6H4-CF2-CH2-NH-SO2-CH(CH3)2 |
| 24 | 6-chloro-3-pyridyl-C(O)NH-C6H4-CHF-CH2-NH-SO2-CH(CH3)2 |

We claim:
1. A compound of the formula:

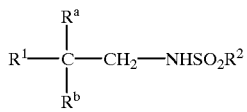

wherein
one or both of $R^a$ and $R^b$ are selected independently from F, $CF_3$ and —$OR^c$ wherein
$R^c$ is hydrogen or (1–4C)alkyl, and any remainder is hydrogen;
$R^1$ represents a phenyl which is unsubstituted or substituted by one or two substituents selected independently from halogen; nitro; cyano; hydroxyimino; (1–10C) alkyl; (2–10C)alkenyl; (2–10C)alkynyl; (3–8C) cycloalkyl; hydroxy(3–8C)cycloalkyl; oxo(3–8C) cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C) alkoxycarbonyldihydrothiazolyl; (1–4C) alkoxycarbonyldimethyidihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH═CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, (1–10C)haloalkyl, (1–4C)alkoxycarbonyl(1–4C)alkyl, (1–4C) alkylsulfonylamino(1–4C)alkyl, (N-(1–4C) alkoxycarbonyl)(1–4C)alkylsulfonylamino-(1–4C) alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^2$ represents (1–6C)alkyl, (1–6C)fluoro-alkyl, (1–6C) chloroalkyl, (2–6C)alkenyl, or (1–4C)alkoxy(1–4C) alkyl; or a pharmaceutically acceptable salt thereof; with the proviso that the compound is other than 1,1,1-trifluoro-N-[2-hydroxy-2-[3-(2-quinolinylmethoxy)phenyl]ethyl]methane sulfonamide.

2. A compound as claimed in claim 1, wherein $R^a$ represents F, $CF_3$ or methoxy and $R^b$ represents hydrogen.

3. A compound as claimed in claim 2, wherein $R^a$ represents methoxy and $R^b$ represents hydrogen.

4. A compound according to claim 3 wherein $R^2$ represents (1–6C)alkyl, (1–6C)fluoroalkyl, or (2–6C)alkenyl.

5. A compound as claimed in claim 4, wherein $R^2$ represents methyl, ethyl, propyl, 2-propyl, butyl, 2-methylpropyl, trifluoromethyl, 2,2,2-trifluoroethyl, chloromethyl, ethenyl, prop-2-enyl, or methoxyethyl.

6. A compound as claimed in claim 5, wherein $R^2$ represents ethyl or 2-propyl.

7. A compound according to claim 6, wherein $R^1$ represents a group of formula

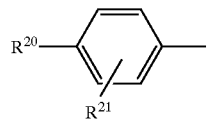

in which
$R^{20}$ represents halogen; nitro; cyano; hydroxyimino; (1–10C)alkyl; (2–10C)alkenyl; (2–10C)alkynyl; (3–8C)cyclo-alkyl; hydroxy(3–8C)cycloalkyl; oxo (3–8C)cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C) cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C) alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C) alkoxycarbonyidihydrothiazolyl; (1–4C) alkoxycarbonyidimethyidihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH═CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen; nitro; cyano; hydroxyimino, (1–10C)alkyl; (2–10C)alkenyl; (2–10C)alkynyl; (3–8C)cycloalkyl; 4-(1,1-dioxotetrahydro-1,2-thiazinyl), halo(1–10C)alkyl; cyano(2–10C)alkenyl, phenyl, $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or NR¹⁹COO, R¹⁵ represents hydrogen, (1–10C)alkyl, phenyl(1–4C)alkyl, (1–10C)haloalkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino(1–4C)alkyl, (3–10C)alkenyl, (3–10C)alkynyl, (3–8C)cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^{21}$ represents a hydrogen atom, a halogen atom, a (1–4C)alkyl group or a (1–4C)alkoxy group.

8. A compound according to claim 1 wherein $R^a$ is F and $R^b$ is hydrogen.

9. A compound according to claim 1 wherein $R^a$ is F and $R^b$ is F.

10. A compound according to claim 8 wherein $R^2$ is isopropyl.

11. A compound according to claim 9 wherein $R^2$ is isopropyl.

12. A compound as claimed in claim 7, wherein $R^1$ represents 4-bromophenyl, 4-benzamidophenyl, 4-methylphenyl, 4-isopropylphenyl, 4-isobutylphenyl, 4-t-butylphenyl, 4-methoxyphenyl, 4-isopropoxyphenyl, 4-cyclopentylphenyl, 4-cyclohexylphenyl, 4-(2-hydroxymethylphenyl)phenyl, 4-(4-hydroxymethylphenyl)phenyl, 4-(2-furyl)phenyl, 4-(3-furyl)phenyl, 4-(2-thienyl)phenyl, 4-(3-thienyl)phenyl, 4-(pyrrolidin-1-yl)phenyl, 4-(piperidin-1-yl)phenyl, 3-chloro-4-piperidin-1-ylphenyl, 4-benzyloxyphenyl, 4-(2-fluorophenyl)phenyl, 4-(3-fluorophenyl)phenyl, 4-(2-formylphenyl)phenyl, 4-(3-formylphenyl)phenyl, 4-(4-formylphenyl)phenyl, 4-(4-methylphenyl)phenyl, 4-(4-hydroxphenyl)phenyl, 4-(2-methoxyphenyl)phenyl or 4-(4-methoxyphenyl)phenyl.

13. A compound selected from the group consisting of:

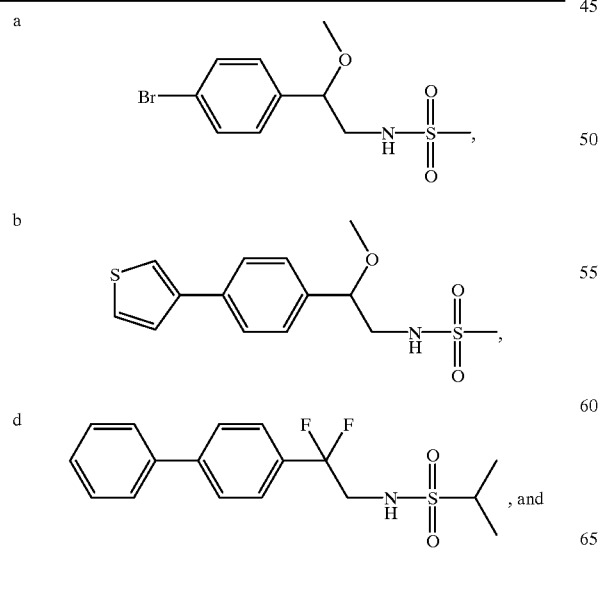

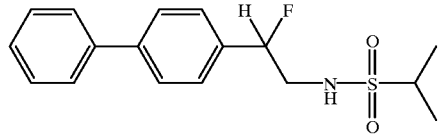

and the pharmaceutically acceptable salts thereof.

14. A pharmaceutical composition, which comprises a compound as claimed in claim 1 and a pharmaceutically acceptable diluent or carrier.

15. A method of potentiating glutamate receptor function in a mammal requiring such treatment, which comprises administering an effective amount of a compound of formula;

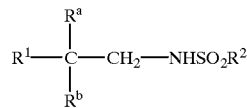

wherein, one or both of $R^a$ and $R^b$ are selected independently from F, $CF_3$ and —$OR^c$ wherein $R^c$ is hydrogen or (1–4C)alkyl, and any remainder is hydrogen;

$R^1$ represents a phenyl which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo(1–10C)alkyl; $(CH_2)_y X^1 R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alkoxycarbonyidihydrothiazolyl; (1–4C)alkoxycarbonyldimethyidihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_z X^3 R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, (1–10C)haloalkyl, (1–4C)alkoxycarbonyl(1–4C)alkyl, (1–4C)alkylsulfonylamino(1–4C)alkyl, (N-(1–4C)alko)$_y$ carbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^2$ represents (1–6C)alkyl, (1–6C)fluoro-alkyl, (1–6C)chloroalkyl, (2–6C)alkenyl, or (1–4C)alkoxy(1–4C)alkyl; or a pharmaceutically acceptable salt thereof.

16. A method of treating a cognitive disorder; a neurodegenerative disorder; age-related dementia; age-induced memory impairment; movement disorder; reversal of a drug-induced state; depression; attention deficit disorder; attention deficit hyperactivity disorder; psychosis; cognitive deficits associated with psychosis; or drug-induced psychosis in a patient, which comprises administering to a patient in need thereof an effective amount of a compound of formula:

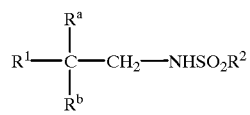

wherein
one or both of $R^a$ and $R^b$ are selected independently from F, $CF_3$ and —$OR^c$ wherein
$R^c$ is hydrogen or (1–4C)alkyl, and any remainder is hydrogen;
$R^1$ represents a phenyl which is unsubstituted or substituted by one or two substitueints selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl; pyrimidinyl; dihydrothienyl; dihydrofuryl; dihydrothiopyranyl; dihydropyranyl; dihydrothiazolyl; (1–4C)alko)$_y$carbonyldihydrothiazolyl; (1–4C)alkoxycarbonyldimethyldihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, NHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, (1–10C)haloalkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^2$ represents (1–6C)alkyl, (1–6C)fluoro-alkyl, (1–6C)chloroalkyl, (2–6C)alkenyl, or (1–4C)alkoxy(1–4C)alkyl; or a pharmaceutically acceptable salt thereof.

17. A method for improving memory or learning ability in a patient, which comprises administering to a patient in need thereof an effective amount of a compound of formula:

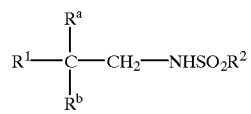

wherein
one or both of $R^a$ and $R^b$ are selected independently from F, $CF_3$ and —$OR^c$ wherein
$R^c$ is hydrogen or (1–4C)alkyl, and any remainder is hydrogen;
$R^1$ represents a phenyl which is unsubstituted or substituted by one or two substituents selected independently from halogen; nitro; cyano; hydroxyimino; (1–10C)alkyl; (2–10C)alkenyl; (2–10C)alkynyl; (3–8C)cycloalkyl; hydroxy(3–8C)cycloalkyl; oxo(3–8C)cycloalkyl; halo(1–10C)alkyl; $(CH_2)_yX^1R^9$ in which y is 0 or an integer of from 1 to 4, $X^1$ represents O, S, $NR^{10}$, CO, COO, OCO, $CONR^{11}$, $NR^{12}CO$, $NR^{12}COCOO$ or $OCONR^{13}$, $R^9$ represents hydrogen, (1–10C)alkyl, (3–10C)alkenyl, (3–10C)alkynyl, pyrrolidinyl, tetrahydrofuryl, morpholino or (3–8C)cycloalkyl and $R^{10}$, $R^{11}$, $R^{12}$ and $R^{13}$ each independently represents hydrogen or (1–10C)alkyl, or $R^9$ and $R^{10}$, $R^{11}$, $R^{12}$ or $R^{13}$ together with the nitrogen atom to which they are attached form an azetidinyl, pyrrolidinyl, piperidinyl or morpholino group; N-(1–4C)alkylpiperazinyl; N-phenyl(1–4C)alkylpiperazinyl; thienyl; furyl; oxazolyl; isoxazolyl; pyrazolyl; imidazolyl; thiazolyl; pyridyl; pyridazinyl;

pyrimidinyl; dihydrothienyl; dihydrofuryl; dihydrothiopyranyl; dihydropyranyl; dihydrothiazolyl; (1–4C)alkoxycarbonyldihydrothiazolyl; (1–4C)alkoxycarbonyidimethyidihydrothiazolyl; tetrahydrothienyl; tetrahydrofuryl; tetrahydrothiopyranyl; tetrahydropyranyl; indolyl; benzofuryl; benzothienyl; benzimidazolyl; and a group of formula $R^{14}$—$(L^a)_n$—$X^2$—$(L^b)_m$ in which $X^2$ represents a bond, O, NH, S, SO, $SO_2$, CO, CH(OH), CONH, NHCO, INHCONH, NHCOO, COCONH, $OCH_2CONH$ or CH=CH, $L^a$ and $L^b$ each represent (1–4C)alkylene, one of n and m is 0 or 1 and the other is 0, and $R^{14}$ represents a phenyl or heteroaromatic group which is unsubstituted or substituted by one or two of halogen, nitro, cyano, hydroxyimino, (1–10C) alkyl, (2–10C)alkenyl, (2–10C)alkynyl, (3–8C)-cycloalkyl, 4-(1,1-dioxotetrahydro-1,2-thiazinyl), halo(1–10C)alkyl, cyano(2–10C)alkenyl, phenyl, and $(CH_2)_zX^3R^{15}$ in which z is 0 or an integer of from 1 to 4, $X^3$ represents O, S, $NR^{16}$, CO, CH(OH), COO, OCO, $CONR^{17}$, $NR^{18}CO$, $NHSO_2$, $NHSO_2NR^{17}$, NHCONH, $OCONR^{19}$ or $NR^{19}COO$, $R^{15}$ represents hydrogen, (1–10C)alkyl, phenyl(1–4C)alkyl, (1–10C)haloalkyl, (1–4C)alkoxycarbonyl(1–4C)alkyl, (1–4C)alkylsulfonylamino(1–4C)alkyl, (N-(1–4C)alkoxycarbonyl)(1–4C)alkylsulfonylamino-(1–4C)alkyl, (3–10C)alkenyl, (3–10C)alkynyl, (3–8C)-cycloalkyl, camphoryl or an aromatic or heteroaromatic group which is unsubstituted or substituted by one or two of halogen, (1–4C)alkyl, halo(1–4C)alkyl, di(1–4C)alkylamino and (1–4C)alkoxy and $R^{16}$, $R^{17}$, $R^{18}$ and $R^{19}$ each independently represents hydrogen or (1–10C)alkyl, or $R^{15}$ and $R^{16}$, $R^{17}$, $R^{18}$ or $R^{19}$ together with the nitrogen atom to which they are attached form an azetidinyl, pyrrolidinyl, piperidinyl or morpholino group; and $R^2$ represents (1–6C)alkyl, (1–6C)fluoro-alkyl, (1–6C)chloroalkyl, (2–6C)alkenyl, or (1–4C)alkoxy(1–4C)alkyl; or a pharmaceutically acceptable salt thereof.

* * * * *